United States Patent

Duggan et al.

[11] Patent Number: 5,925,655
[45] Date of Patent: Jul. 20, 1999

[54] $\alpha_V\beta_3$ ANTAGONISTS

[75] Inventors: Mark E. Duggan, Schwenksville; George D. Hartman; William F. Hoffman, both of Lansdale, all of Pa.

[73] Assignee: Merck & Co., Inc., Rahway, N.J.

[21] Appl. No.: 08/841,979

[22] Filed: Apr. 8, 1997

Related U.S. Application Data

[60] Provisional application No. 60/015,177, Apr. 10, 1996.

[51] Int. Cl.⁶ .................. C07D 401/14; C07D 209/46; A61K 31/40
[52] U.S. Cl. .................. 514/333; 514/339; 546/256; 546/277.1
[58] Field of Search ................ 546/256, 277.1; 514/333, 339

[56] References Cited

U.S. PATENT DOCUMENTS 4,505,911 3/1985 Dolak et al. ........................ 514/229
5,416,099 5/1995 Hartman et al. ...................... 514/323
5,491,232 2/1996 Patsch et al. ........................ 544/3

OTHER PUBLICATIONS

Omenn, Cancer Prevention, Cecil Textbook of Medicine, 20th Edition, vol. 1, pp. 1008–1010, 1996.

*Primary Examiner*—Richard L. Raymond
*Assistant Examiner*—Deepak R. Rao
*Attorney, Agent, or Firm*—Philippe L. Durette; Anthony D. Sabatelli; Melvin Winokur

[57] ABSTRACT

This invention relates to certain novel isoindolone compounds and derivatives thereof, their synthesis, and their use as $\alpha v\beta 3$ receptor antagonists. The $\alpha v\beta 3$ receptor antagonist compounds of this invention are useful for inhibiting bone resorption, treating and preventing osteoporosis and cancer, and inhibiting vascular restenosis, diabetic retinopathy, macular degeneration, angiogenesis, atherosclerosis, inflammation and tumor growth.

18 Claims, No Drawings

$\alpha_v\beta_3$ ANTAGONISTS

CROSS REFERENCE TO RELATED APPLICATIONS

This application claims priority to U.S. provisional patent application Ser. No. 60/015,177, filed Apr. 10, 1996.

FIELD OF THE INVENTION

The present invention provides novel compounds and derivatives thereof, their synthesis, and their use as αvβ3 ligands. More particularly, the compounds of the present invention are useful for inhibiting bone resorption, treating and preventing osteoporosis and cancer, and inhibiting vascular restenosis, diabetic retinopathy, macular degeneration, angiogenesis, atherosclerosis, inflammation and tumor growth.

BACKGROUND OF THE INVENTION

This invention relates to compounds for inhibiting bone resorption that is mediated by the action of a class of cells known as osteoclasts.

Osteoclasts are multinucleated cells of up to 400 μm in diameter that resorb mineralized tissue, chiefly calcium carbonate and calcium phosphate, in vertebrates. They are actively motile cells that migrate along the surface of bone. They can bind to bone, secrete necessary acids and proteases and thereby cause the actual resorption of mineralized tissue from the bone.

More specifically, osteoclasts are believed to exist in at least two physiological states. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they attach again to bone.

Integrins are transmembrane, heterodimeric, glycoproteins which interact with extracellular matrix and are involved in osteoclast attachment, activation and migration. The most abundant integrin in osteoclasts (rat, chicken, mouse and human) is the vitronectin receptor, or αvβ3, thought to interact in bone with matrix proteins that contain the RGD sequence. Antibodies to αvβ3 block bone resorption in vitro indicating that this integrin plays a key role in the resorptive process. There is increasing evidence to suggest that αvβ3 ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment.

All these conditions are characterized by bone loss, resulting from an imbalance between bone resorption (breakdown) and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, αvβ3 ligands have been found to be useful in treating and/or inhibiting restenosis (recurrence of stenosis after corrective surgery on the heart valve), atherosclerosis, inflammation, diabetic retinopathy, macular degeneration and angiogenesis (formation of new blood vessels). Moreover, it has been postulated that the growth of tumors depends on an adequate blood supply, which in turn is dependent on the growth of new vessels into the tumor; thus, inhibition of angiogenesis can cause tumor regression in animal models. (See, *Harrison's Principles of Internal Medicine*, 12th ed., 1991). αvβ3 antagonists, which inhibit angiogenesis, are therefore useful in the treatment of cancer for inhibiting tumor growth. (See e.g., Brooks et al., *Cell*, 79:1157–1164 (1994)).

It is an object of the present invention to identify compounds which bind to the αvβ3 receptor.

It is a further object of the invention to identify compounds which act as antagonists of the αvβ3 receptor. It is another object of the invention to identify αvβ3 antagonist compounds which are useful agents for inhibiting: bone resorption mediated by osteoclast cells, restenosis, atherosclerosis, inflammation, diabetic retinopathy, macular degeneration and angiogenesis in animals, preferably mammals, especially humans. Still another object of the invention is to identify αvβ3 antagonists which cause tumor regression and/or inhibit tumor growth in animals.

A further object of the invention is to identify αvβ3 antagonists useful for preventing or treating osteoporosis. An additional object of the invention is to identify αvβ3 antagonists useful for treating cancer.

It has now been found that the compounds of the present invention, αvβ3 ligands, are useful for inhibiting osteoclast mediated bone resorption in mammals. Thus, the compounds of the present invention are useful for preventing or reducing the incidence of osteoporosis. Additionally, it has been found that the αvβ3 ligands of the present invention are also useful for treating and/or inhibiting restenosis, cancer, tumor growth, diabetic retinopathy, macular degeneration, atherosclerosis, inflammation and/or angiogenesis in mammals.

SUMMARY OF THE INVENTION

The present invention provides compounds of the formula

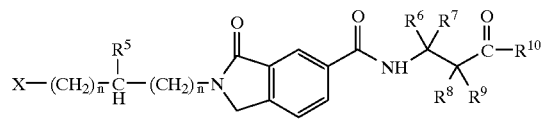

wherein X is selected from

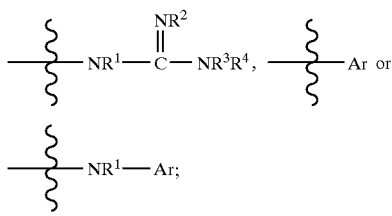

Ar is a 4- to 10-membered mono- or polycyclic aromatic or non-aromatic ring system containing 0, 1, 2, 3 or 4 heteroatoms selected from N, O or S and wherein the mono- or polycyclic aromatic or non-aromatic ring system is either unsubstituted or substituted with $R^1$, $R^2$, $R^3$ and $R^4$;

$R^1$, $R^2$, $R^3$ and $R^4$ are each independently selected from hydrogen, hydroxyl, $C_{1-8}$ alkyl, halogen, aryl $C_{0-8}$ alkyl, oxo, thio, amino-$C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, aryl $C_{0-6}$ alkylamino $C_{0-6}$ alkyl, $C_{1-4}$ alkoxyamino $C_{0-8}$ alkyl, hydroxy $C_{1-6}$ alkylamino $C_{0-8}$ alkyl, $C_{1-4}$ alkoxy $C_{0-8}$ alkyl, carboxy $C_{0-8}$ alkyl, $C_{1-4}$ alkoxycarbonyl-$C_{0-8}$ alkyl, carboxy $C_{0-8}$ alkoxy, hydroxy $C_{0-8}$ alkyl or $C_{3-8}$ cycloalkyl $C_{0-6}$ alkyl;

$R^5$ is selected from hydrogen, $C_{1-6}$ alkyl, $C_{0-6}$ alkylaryl, aryl or $C_{3-8}$ cycloalkyl $C_{0-6}$ alkyl;

$R^6$, $R^7$, $R^8$ and $R^9$ are each independently selected from hydrogen, fluorine, $C_{1-8}$ alkyl, hydroxyl, hydroxy $C_{1-6}$ alkyl, carboxy-$C_{0-6}$ alkyl, $C_{1-6}$ alkoxy, $C_{1-6}$ alkylcarbonyl, aryl $C_{0-6}$ alkylcarbonyl, $C_{1-6}$ alkylcarbonyloxy, aryl $C_{0-6}$ alkylcarbonyloxy, $C_{1-6}$ alkylaminocarbonyloxy, $C_{3-8}$ cycloallyl, aryl $C_{0-6}$ alkyl, $C_{0-6}$ alkylamino-$C_{0-6}$ alkyl, $C_{0-6}$ dialkylamino $C_{0-6}$ alkyl, $C_{1-8}$ alkylsulfonylamino-$C_{0-6}$ alkyl, aryl $C_{0-6}$ alkylsulfonylamino $C_{0-6}$ alkyl, $C_{0-8}$ alkyl-$SO_2NR^3$—$C_{0-8}$ alkyl, aryl $C_{0-8}$ alkoxycarbonylamino $C_{0-8}$ alkyl, aryl $C_{0-8}$ alkyl-$SO_2NR^3$—$C_{0-8}$ alkyl, $C_{1-8}$ alkoxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{3-8}$ cycloalkyl $C_{0-6}$ alkyl, $C_{3-8}$ cycloalkyl $C_{0-6}$ alkylsulfonylamino $C_{0-6}$ akyl, $C_{3-8}$ cycloalkyl $C_{0-6}$ alkylcarbonyl, $C_{3-8}$ cycloalkyl $C_{0-6}$ alkylaminocarbonyloxy or $C_{3-8}$ cycloalkyl $C_{0-6}$ alkylaminocarbonylamino; wherein any of the alkyl groups may be unsubstituted or substituted with $R^1$ and $R^2$;

$R^{10}$ is selected from hydroxyl, $C_{1-8}$ alkoxy, aryl $C_{0-6}$ alkoxy, $C_{1-8}$ alkylcarbonyloxy $C_{1-4}$ alkoxy, aryl $C_{1-8}$ alkylcarbonyloxy $C_{1-4}$ alkoxy, $C_{1-8}$ dialkylaminocarbonylmethoxy, aryl $C_{1-6}$ dialkylaminocarbonylmethoxy or an L- or D-amino acid joined by an amide linkage and wherein the carboxylic acid moiety of the amino acid is as the free acid or is esterified by $C_{1-6}$ alkyl; and each n is independently an integer from 0 to three;

provided that when $R^5$ is hydrogen and X is Ar and Ar is a 6-membered monocyclic non-aromatic ring system containing one nitrogen atom and $R^6$ and $R^7$ are each hydrogen, and $R^8$ is selected from hydrogen or $C_{1-6}$ alkyl, and $R^{10}$ is selected from hydroxyl, $C_{1-8}$ alkoxy, $C_{1-8}$ alkylcarbonyloxy $C_{1-4}$ alkoxy or an L- or D-amino acid joined by an amide linkage and wherein the carboxylic acid moiety of the amino acid is as the free acid or is esterified with $C_{1-6}$ alkyl, then $R^9$ is selected from fluorine, hydroxyl, hydroxy $C_{1-6}$ alkyl, carboxy $C_{0-6}$ alkyl, $C_{0-6}$ alkoxy, $C_{1-6}$ alkylcarbonyl, aryl $C_{0-6}$ alkylcarbonyl, $C_{1-6}$ alkylcarbonyloxy, aryl $C_{0-6}$ alkylcarbonyloxy, $C_{1-6}$ alkylaminocarbonyloxy, $C_{3-9}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, aryl $C_{0-8}$ alkoxycarbonylamino $C_{0-8}$ alkyl, $C_{1-8}$ alkoxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{3-8}$ cycloalkyl $C_{0-6}$ alkyl, $C_{3-8}$ cycloalkyl $C_{0-6}$ alkylsulfonylamino $C_{0-6}$ akyl, $C_{3-8}$ cycloalkyl $C_{0-6}$ alkylcarbonyl, $C_{3-8}$ cycloalkyl $C_{0-6}$ alkylaminocarbonyloxy or $C_{3-8}$ cycloalkyl $C_{0-6}$ alkylaminocarbonylamino; wherein any of the alkyl groups may be unsubstituted or substituted with $R^1$ and $R^2$;

and provided further that when $R^5$ is hydrogen and X is Ar and Ar is

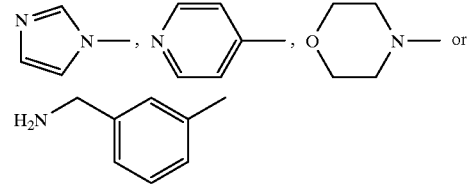

and $R^6$, $R^7$ and $R^8$ are each hydrogen, and $R^{10}$ is selected from hydroxyl and $C_{1-8}$ alkoxy, then $R^9$ is selected from fluorine, $C_{1-8}$ alkyl, hydroxyl, hydroxy $C_{1-6}$ alkyl, carboxy $C_{0-6}$ alkyl, $C_{1-6}$ alkoxy, $C_{1-6}$ alkylcarbonyl, aryl $C_{0-6}$ alkylcarbonyl, $C_{1-6}$ alkylcarbonyloxy, aryl $C_{0-6}$ alkylcarbonyloxy, $C_{1-6}$ alkylaminocarbonyloxy, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, $C_{0-8}$ alkyl-$SO_2NR^3C_{0-8}$ alkyl, aryl $C_{0-8}$ alkoxycarbonylamino $C_{0-8}$ alkyl, $C_{1-8}$ alkoxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{3-8}$ cycloalkyl $C_{0-6}$ alkyl, $C_{3-8}$ cycloalkyl $C_{0-6}$ alkylsulfonylamino $C_{0-6}$ akyl, $C_{3-8}$ cycloalkyl $C_{0-6}$ alkylcarbonyl, $C_{3-8}$ cycloalkyl $C_{0-6}$ alkylaminocarbonyloxy or $C_{3-8}$ cycloalkyl $C_{0-6}$ alkylaminocarbonylamino; wherein any of the alkyl groups may be unsubstituted or substituted with $R^1$ and $R^2$; and the pharmaceutically acceptable salts thereof.

In one embodiment of the invention is the compound wherein Ar is selected from

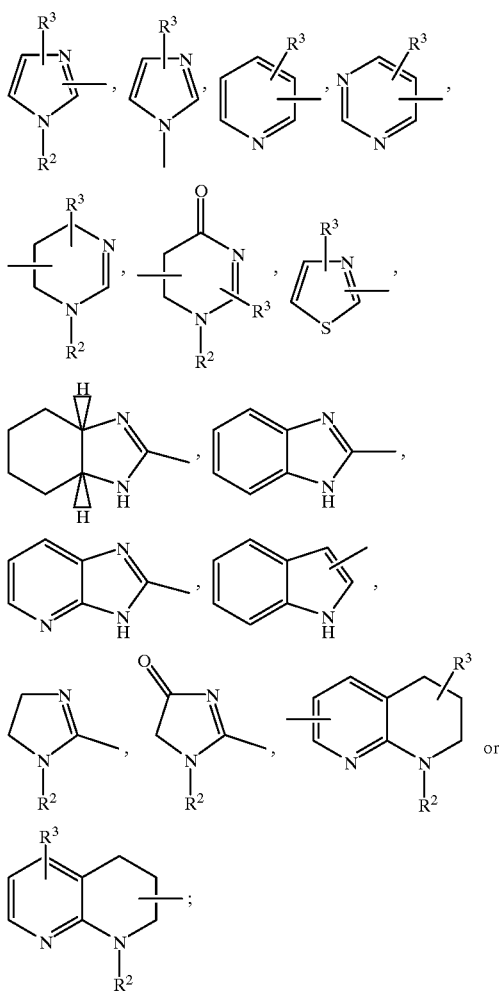

where all other variables are as defined above;
provided that when when $R^5$ is hydrogen and X is Ar and Ar is

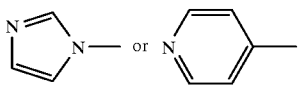

and $R^6$, $R^7$ and $R^8$ are each hydrogen, and $R^{10}$ is selected from hydroxyl and $C_{1-8}$ alkoxy, then $R^9$ is selected from fluorine, $C_{1-8}$ alkyl, hydroxyl, hydroxy $C_{1-6}$ alkyl, carboxy $C_{0-6}$ alkyl, $C_{1-6}$ alkoxy, $C_{1-6}$ alkylcarbonyl, aryl $C_{0-6}$ alkylcarbonyl, $C_{1-6}$ alkylcarbonyloxy, aryl $C_{0-6}$ alkylcarbonyloxy, $C_{1-6}$ alkylaminocarbonyloxy, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, $C_{0-8}$ alkyl-$SO_2NR^3$—$C_{0-8}$ alkyl, aryl $C_{0-8}$ alkoxycarbonylamino $C_{0-8}$ alkyl, $C_{1-8}$ alkoxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{3-8}$ cycloalkyl $C_{0-6}$ alkyl, $C_{3-8}$ cycloalkyl $C_{0-6}$ alkylsulfonylamino $C_{0-6}$ alkyl, $C_{3-8}$ cycloalkyl $C_{0-6}$ alkylcarbonyl, $C_{3-8}$ cycloalkyl $C_{0-6}$ alkylaminocarbonyloxy or $C_{3-8}$ cycloalkyl $C_{0-6}$ alkylaminocarbonylamino; wherein any of the alkyl groups may be unsubstituted or substituted with $R^1$ and $R^2$;

and the pharmaceutically acceptable salts thereof.

In a class of this first embodiment is the compound wherein $R^1$, $R^2$, $R^3$ and $R^4$ are each independently selected from hydrogen, $C_{1-6}$ alkyl, aryl $C_{0-6}$ alkyl, amino $C_{0-6}$ alkyl, $C_{1-6}$ alkylamino $C_{0-6}$ alkyl, $C_{1-6}$ dialkylamino $C_{0-6}$ alkyl, $C_{1-4}$ alkoxy $C_{0-6}$ alkyl, $C_{1-4}$ alkoxycarbonyl $C_{0-6}$ alkyl;

$R^6$, $R^7$, $R^8$ and $R^9$ are each independently selected from hydrogen, $C_{1-6}$ alkyl, $C_{0-6}$ alkylamino $C_{0-6}$ alkyl, $C_{0-6}$ dialkylamino $C_{0-6}$ alkyl, aryl $C_{0-6}$ alkoxycarbonylamino $C_{0-6}$ alkyl, aryl $C_{0-6}$ alkyl-$SO_2NR^3$—$C_{0-6}$ alkyl, $C_{0-6}$ alkyl-$SO_2NR^3$—$C_{0-6}$ alkyl or aryl $C_{0-6}$ alkylcarbonylamino $C_{0-6}$ alkyl;

$R^{10}$ is selected from hydroxy, $C_{1-8}$ alkoxy, $C_{1-6}$ dialkylaminocarbonylmethoxy or aryl $C_{1-6}$ dialkylaminocarbonylmethoxy; where all other variables are as defined above;

provided that when when $R^5$ is hydrogen and X is Ar and Ar is

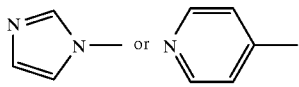

and $R^6$, $R^7$ and $R_8$ are each hydrogen, and $R^{10}$ is selected from hydroxyl and $C_{1-8}$ alkoxy, then $R^9$ is selected from hydrogen, $C_{1-6}$ alkyl, $C_{0-6}$ alkylamino $C_{0-6}$ alkyl, $C_{0-6}$ dialkylamino $C_{0-6}$ alkyl, aryl $C_{0-6}$ alkoxycarbonylamino $C_{0-6}$ alkyl, $C_{0-6}$ alkyl-$SO_2NR^3$—$C_{0-6}$ alkyl or aryl $C_{0-6}$ alkylcarbonylamino $C_{0-6}$ alkyl;

and the pharmaceutically acceptable salts thereof.

In a second embodiment of the invention is the compound wherein X is selected from

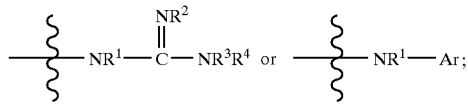

where all other variables are as defined above; and the pharmaceutically acceptable salts thereof.

In a class of this second embodiment is the compound wherein Ar is selected from

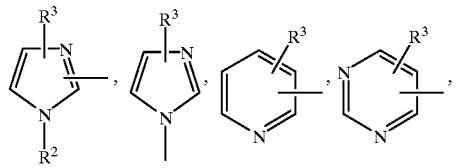

-continued

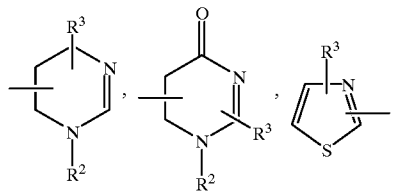

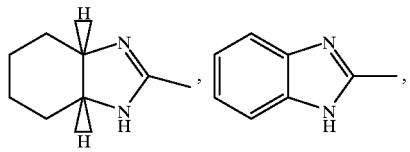

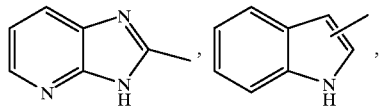

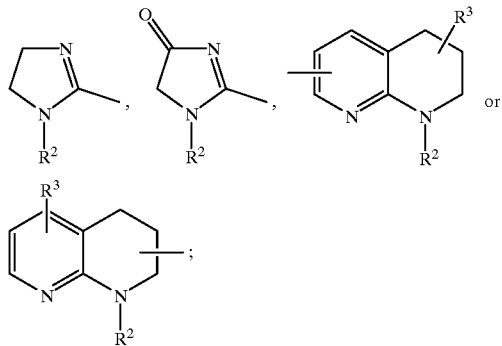

$R^1$, $R^2$, $R^3$ and $R^4$ are each independently selected from hydrogen, $C_{1-6}$ alkyl, aryl $C_{0-6}$ alkyl, amino $C_{0-6}$ alkyl, $C_{1-6}$ alkylamino $C_{0-6}$ alkyl, $C_{1-6}$ dialkylamino $C_{0-6}$ alkyl, $C_{1-4}$ alkoxy $C_{0-6}$ alkyl, $C_{1-4}$ alkoxycarbonyl $C_{0-6}$ alkyl;

$R^6$, $R^7$, $R^8$ and $R^9$ are each independently selected from hydrogen, $C_{1-6}$ alkyl, $C_{0-6}$ alkylamino $C_{0-6}$ alkyl, $C_{0-6}$ dialkylamino $C_{0-6}$ alkyl, aryl $C_{0-6}$ alkoxycarbonylamino $C_{0-6}$ alkyl, aryl $C_{0-6}$ alkyl-$SO_2NR^3$—$C_{0-6}$ alkyl, $C_{0-6}$ alkyl-$SO_2NR^3$—$C_{0-6}$ alkyl or aryl $C_{0-6}$ alkylcarbonylamino $C_{0-6}$ alkyl;

$R^{10}$ is selected from hydroxy, $C_{1-8}$ alkoxy, $C_{1-6}$ dialkylaminocarbonylmethoxy or aryl $C_{1-6}$ dialkylaminocarbonylmethoxy;

where all other variables are as defined above;

and the pharmaceutically acceptable salts thereof.

In a subclass of this second embodiment is the compound of the formula

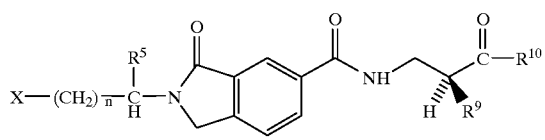

wherein Ar is selected from

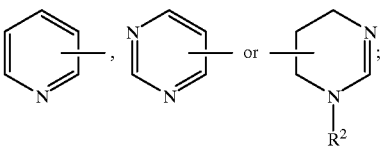

$R^1$, $R^2$, $R^3$ and $R^4$ are each independently selected from hydrogen or $C_{1-6}$ alkyl;

$R^5$ is selected from hydrogen or $C_{1-6}$ alkyl;

$R^9$ is selected from

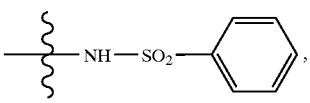

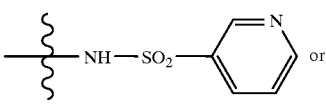

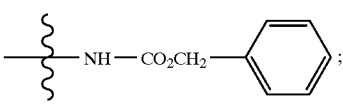

$R^{10}$ is selected from hydrogen or $C_{1-6}$ alkoxy; and n is an integer from 0 to 3;

and the pharmaceutically acceptable salts thereof.

Illustrative of this second embodiment is the compound wherein X is selected from

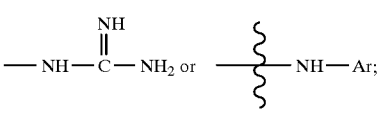

Ar is selected from

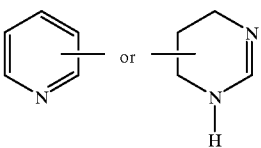

$R^5$ is selected from hydrogen or methyl; and n is an integer from 1 to 2; and wherein all other variables are as defined above; and the pharmaceutically acceptable salts thereof.

Exemplifying this second embodiment of the invention is the compound wherein Ar is selected from

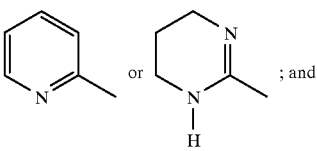

$R^{10}$ is hydroxy;

and wherein all other variables are as defined above; and the pharmaceutically acceptable salts thereof.

An illustration of the invention is the compound selected from

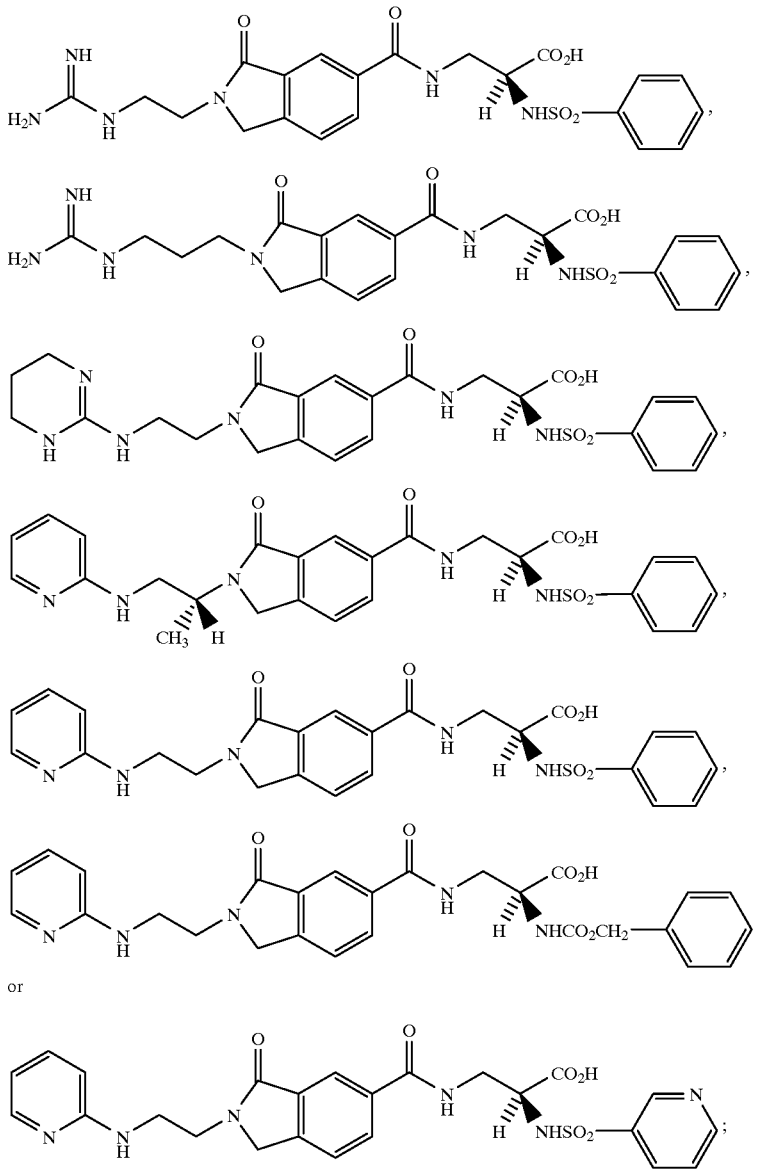

and the pharmaceutically acceptable salts thereof.

Illustrating the invention is a pharmaceutical composition comprising any of the compounds described above and a pharmaceutically acceptable carrier. An example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Another example of the invention is a method of eliciting an αvβ3 antagonizing effect in a mammal in need thereof, comprising administering to the mammal a therapeutically effective amount of any of the compounds or any of the pharmaceutical compositions described above. Preferably, the αvβ3 antagonizing effect is selected from inhibition of bone resorption, inhibition of restenosis, inhibition of atherosclerosis, inhibition of inflammation, inhibition of aniogenesis, inhibition of diabetic retinopathy, inhibition of macular degeneration or inhibition of tumor growth. Most preferably, the αvβ3 antagonizing effect is inhibition of bone resorption.

Further illustrating the invention is a method of treating and/or preventing a condition mediated by an αvβ3 receptor in a mammal in need thereof, comprising administering to the mammal a therapeutically effective amount of any of the compounds or any of the pharmaceutical compositions described above. Preferably, the condition is selected from osteoporosis, cancer, bone resorption, restenosis, diabetic retinopathy, macular degeneration, atherosclerosis, inflammation, angiogenesis or tumor growth. More preferably, the condition is selected from osteoporosis or cancer. Most preferably, the condition is osteoporosis.

Another illustration of the invention is a method of inhibiting bone resorption in a mammal in need thereof, comprising administering to the mammal a therapeutically effective amount of any of the compounds or any of the pharmaceutical compositions decribed above.

Another example of the invention is a method of treating and/or preventing osteoporosis in a mammal in need thereof, comprising administering to the mammal a therapeutically effective amount of any of the compounds or any of the pharmaceutical compositions decribed above.

Further exemplifying the invention is any of the compositions described above, further comprising a therapeutically effective amount of a second bone resorption inhibitor; preferably, the second bone resorption inhibitor is alendronate.

More particularly illustrating the invention is any of the methods of treating and/or preventing osteoporosis and/or of inhibiting bone resorption described above, wherein the compound is administered in combination with a second bone resorption inhibitor; preferably, the second bone resorption inhibitor is alendronate.

Additional examples of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More specifically exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone resorption, tumor growth, cancer, restenosis, atherosclerosis, inflammation, diabetic retinopathy, macular degeneration and/or angiogenesis.

DETAILED DESCRIPTION OF THE INVENTION

Representative compounds of the present invention are $\alpha v\beta 3$ antagonists which display submicromolar affinity for the human $\alpha v\beta 3$ receptor. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit: the activity of mammalian osteoclasts, restenosis, tumor growth, atherosclerosis, inflammation, macular degeneration, diabetic retinopathy and angiogenesis.

The compounds of the present invention are administered in dosages effective to antagonize the $\alpha v\beta 3$ receptor where such treatment is needed, as, for example, in the prevention or treatment of osteoporosis. For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a mono- or polycyclic system composed of 5- and 6-membered aromatic rings containing 0, 1, 2, 3 or 4 heteroatoms chosen from N, O or S and either unsubstituted or substituted with $R^1$ and $R^2$. Examples of aryl include, but are not limited to, phenyl, naphthyl, pyridyl, pyrimidinyl, imidazolyl, benzimidazolyl, indolyl, thienyl, oxazolyl, isoxazolyl and thiazolyl, which are either unsubstituted or substituted with $R^1$ and $R^2$.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. The $C_{0-m}$ or $C_{1-m}$ designation where m may be an integer from 1–10 or 2–10 respectively refers to the alkyl component of the arylalkyl or alkylaryl unit. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

When substituent $R^1, R^2, R^3, R^4, R^5, R^6, R^7, R^8, R^9$ or $R^{10}$ includes the definition $C_0$ (e.g., aryl $C_{0-8}$ alkyl), the group modified by $C_0$ is not present in the substituent.

The term "halogen" shall include iodine, bromine, chlorine and fluorine.

The term "oxy" means an oxygen (O) atom. The term "thio" means a sulfur (S) atom. The term "oxo" shall mean =O.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

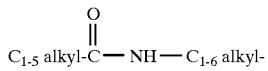

The present invention is also directed to combinations of the compounds of the present invention with one or more agents useful in the prevention or treatment of osteoporosis. For example, the compounds of the instant invention may be effectively administered in combination with effective amounts of other agents used in the treatment of osteoporosis such as the bone resorption inhibitor alendronate, now sold as FOSAMAX®. Preferred combinations are simultaneous or alternating treatments of an αvβ3 receptor antagonist of the present invention and FOSAMAX®. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating αvβ3 related conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous or intramuscular form, all using forms well known to those of ordinary skill in the pharmaceutical arts. An effective but non-toxic amount of the compound desired can be employed as an αvβ3 inhibitor.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 1.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose. methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the schemes and examples below, various reagent symbols and abbreviations have the following meanings:
BH₃•DMS: Borane•dimethylsulfide.
BOC(Boc): t-butyloxycarbonyl.
BOP: Benzotriazol-1-yloxytris(dimethylamino)-phosphonium hexafluorophosphate.
CBZ(Cbz): Carbobenzyloxy or benzyloxycarbonyl.
CDI: Carbonyldiimidazole.
CH₂Cl₂: Methylene chloride.
CHCl₃: Chloroform.
DEAD: Diethyl azodicarboxylate.
DIAD: Diisopropyl azodicarboxylate.
DIBAH or DIBAL-H: Diisobutylaluminum hydride.
DIPEA: Diisopropylethylamine.
DME: 1,2-Dimethoxyethane.
DMF: Dimethylformamide.
DMSO: Dimethylsulfoxide.
DPFN: 3,5-Dimethyl-1-pyrazolylformamidine nitrate.

EDC: 1-(3-Dimethylaminopropyl)-3-ethylcarbodiimide.
EtOAc: Ethyl acetate.
EtOH: Ethanol.
HOAc: Acetic acid.
HOBT: 1-Hydroxybenzotriazole.
LDA: Lithium diisopropylamide.
MeOH: Methanol.
NEt₃: triethylamine.
NMM: N-methylmorpholine.
PCA•HCl: Pyrazole carboxamidine hydrochloride.
Pd/C: Palladium on activated carbon catalyst.
Ph: Phenyl.
TEA: Triethylamine.
TFA: Trifluoroacetic acid.
THF: Tetrahydrofuran.
TLC: Thin Layer Chromatography The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making preferred compounds of the present invention. Moreover, by utilizing the procedures described in detail in PCT International Application Publication Nos. WO95/32710, published Dec. 7 1995, and WO95/17397, published Jun. 29, 1995, in conjunction with the disclosure contained herein, one of ordinary skill in the art can readily prepare additional compounds of the present invention claimed herein.

SCHEME 1

L-asparagine

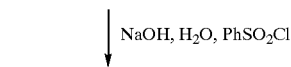

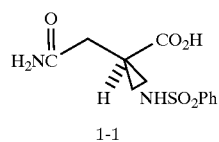

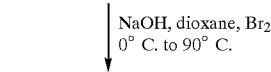

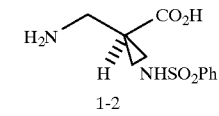

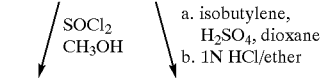

-continued

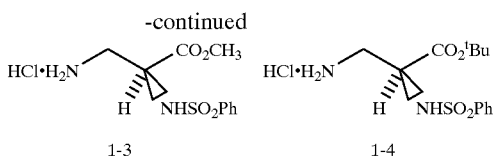

N-Phenylsulfonyl-L-asparagine (1-1)

To a stirred solution of L-asparagine (Aldrich) (10 g, 76 mmol), NaOH (3.4 g, 85 mmol), $H_2O$ (50 mL), and dioxane (50 mL) at 0° C. was added $PhSO_2Cl$ (10.6 mL, 84 mmol). After 1 min, NaOH (3.4 g) in $H_2O$ (50 mL) was added and the reaction mixture stirred for 30 min. The reaction mixture was then concentrated to remove the dioxane then washed with EtOAc. The aqueous phase was then cooled to 0° C. and acidified to pH 5.0 with conc. HCl to effect product precipitation. The resulting solid was collected by filtration, washed with $H_2O$ (20 mL) and dried at 50° C. under vacuum to give N-phenylsulfonyl-L-asparagine (1-1) as a white solid.

$R_f$ 0.40 (silica, 10:1:1 ethanol/$H_2O$/$NH_4OH$). $^1H$ NMR (300 MHz, $D_2O$) δ7.59 (m, 2H), 7.26 (m, 3H), 3.92 (m, 1H), 3.02 (m, 1H), 2.35 (m, 1H).

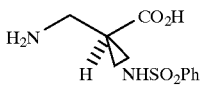

3-Amino-2(S)-phenylsulfonylaminopropionic acid (1-2)

To stirred solution of NaOH (15.6 g, 0.4 mol) in $H_2O$ (70 mL), cooled with an icebath, was added bromine (3.6 mL, 0.07 mol) dropwise. After 5 min, a cold solution of N-phenylsulfonyl-L-asparagine, 1-1 (14.6 g, 54 mmol) and NaOH (4.3 g, 0.1 mol) in $H_2O$ (50 mL) was added in one portion. The solution was stirred for 20 min at 0° C. then 30 min at 90° C. The reaction mixture was recooled to 0° C., and the pH adjusted to 7 through dropwise addition of conc. HCl. The white precipitate formed was collected by filtration and then dried to give (1-2) as a white solid.

$^1H$ NMR (300 MHz, $D_2O$) δ 8.00–7.50 (m, 5H), 3.88 (m, 1H), 3.37 (m, 1H), 3.12 (m, 1H).

Methyl 3-Amino-2(S)-phenylsulfonylaminopropionate hydrochloride (1-3)

To a stirred solution of 1-2 (5.0 g, 21 mmol) in $CH_3OH$ (100 mL) at 0° C. was added $SOCl_2$ (7.5 mL, 100 mmol) dropwise. The cooling bath was then removed and the solution stirred at ambient temperature for 20 h. Concentration and trituration with ether gave 1-3 as a white solid.

$^1H$ NMR (300 MHz, $D_2O$) δ7.82–7.50 (m, 5H), 4.32 (m, 1H), 3.40 (m, 1H), 3.32 (s, 3H), 3.10 (m, 1H).

tert-Butyl 3-Amino-2(S)-phenylsulfonylaminopropionate hydrochloride (1-4)

In a Fischer-Porter tube, a mixture of 1-2 (10.2 g, 42 mmol) and DME (150 mL) was sequentially treated with $H_2SO_4$ (6.4 mL, 0.12 mol), cooled to −78° C., and then condensed isobutylene (75 mL). The cooling bath was removed. After 24 h, ice/water (250 mL) was added followed by washing with ether (2x). The aqueous phase was basified with aq 6 N NaOH, then saturated with NaCl, followed by extraction with EtOAc (3x). The combined extracts were washed with brine, dried ($MgSO_4$), and concentrated to give a white solid. This was dissolved in $CH_2Cl_2$ and treated with 1 N HCl/ether (22 mL), and then concentrated to give 1-4 as a glassy yellow solid.

$^1H$ NMR (400 MHz, DMSO) δ8.25–8.00 (m, 4H), 7.85–7.58 (m, 5H), 4.08 (m, 1H), 3.10 (m, 1H), 2.73 (m, 1H), 1.17 (s, 9H).

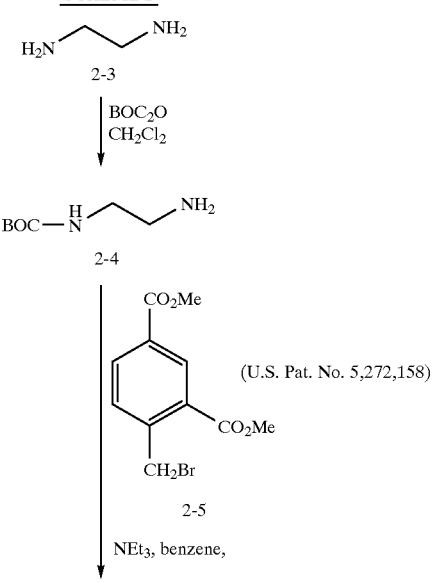

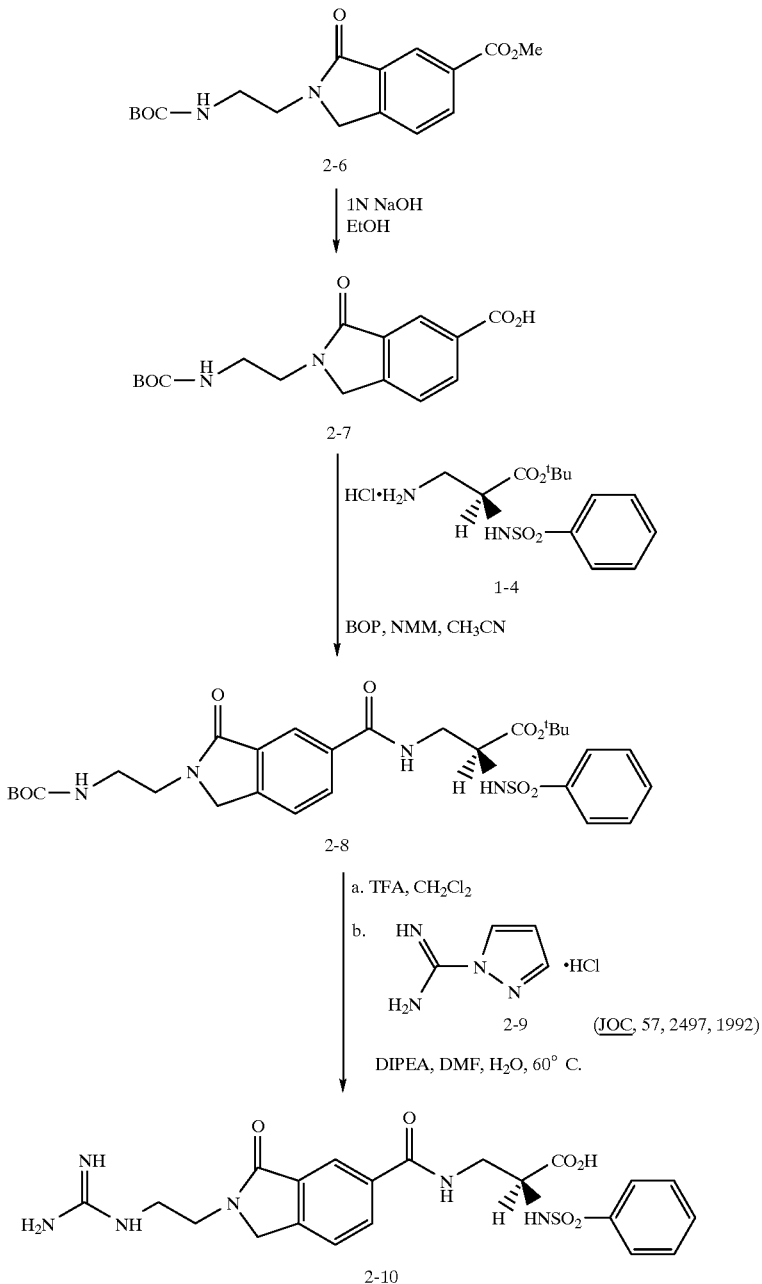

N-t-Butyloxycarbonyl-1,2-diaminoethane (2-4)

To a stirred solution of 1,2-diaminoethane 2-3 (50 g, 832 mmol) and $CH_2Cl_2$ (500 ml) was added a solution of $BOC_2O$ (45 g, 208 mmole) in $CH_2Cl_2$ (100 ml) dropwise over a 3 h period. After 20 h, the reaction was filtered and then the filtrate was concentrated at 60° C. to furnish amine 2-4 as a colorless oil.

$^1H$ NMR (300 MHz, $CDCl_3$) 4.94 (bs, 1H), 3.16 (m, 2H), 2.80 (t, J=6 Hz, 2H), 1.45 (s, 9H), 1.16 (s, 2H).

Methyl-[2-(N-t-butyloxycarbonylamino)ethyl]-1-isoindolone-6-carboxylate (2-6)

A solution of amine 2-4 (386 mg, 2.41 mmole), bromide 2-5 (692 mg, 2.41 mmole), $NEt_3$ (990 μl, 7.23 mmole) and benzene (10 ml) was heated at reflux for 20 h. The reaction was diluted with ethyl acetate and then washed with $H_2O$, sat. $NaHCO_3$, 10% $KHSO_4$, brine, dried ($MgSO_4$) and concentrated. Flash chromatography (silica, EtOAc) gave the ester 2-6 as a yellow solid.

TLC $R_f$=0.24 (ethyl acetate); $^1H$ NMR (400 MHz, $CD_3OD$) 8.49 (s, 1H), 8.36 (dd, J=2 Hz, 8 Hz, 1H), 7.80 (d, J=8 Hz, 1H), 4.99 (s, 2H), 4.07 (s, 3H), 3.84 (t, J=5 Hz, 2H), 3.49 (t, J=6 Hz, 2H), 1.42 (s, 9H).

[2-(N-t-Butyloxycarbonylamino)ethyl]-1-isoindolone-6-carboxylic acid (2-7)

A solution of ester 2-6 (480 mg, 1.44 mmole), 1 N NaOH (3.0 ml, 3.0 mmoles) and EtOH (5 ml) was stirred at ambient temperature for 5.0 h. The reaction was acidified with 10% $KHSO_4$ and then extracted with EtOAc. The EtOAc portion was washed with brine, dried ($MgSO_4$) and concentrated to furnish the carboxylic acid 2-7 as a yellow solid.

¹H NMR (400 MHz, CD₃OD) 8.52 (s, 1H), 8.37 (dd, J=1 Hz, 8 Hz, 1H), 7.79 (d, J=8 Hz, 1H), 4.77 (s, 2H), 3.85 (t, J=6 Hz, 2H), 3.50 (t, J=6 Hz, 2H), 1.43 (s, 9H).

[2-(N-t-Butyloxycarbonylamino)ethyl]-1-isoindolone-6-carbonyl-2(S)-phenylsulfonyl)amino-β-alanine t-butyl ester (2-8)

A solution of acid 2-7 (380 mg, 1.19 mmole), amine 1-4 (362 mg, 1.19 mmole), BOP (789 mg, 1.79 mmole), NMM (521 μl, 4.76 mmole) and CH₃CN (6 ml) was stirred at ambient temperature for 20 h. The reaction was diluted with ethyl acetate and then washed with H₂O, sat. NaHCO₃, 10% KHSO₄, brine, dried (MgSO₄) and concentrated. Flash chromotography (silica, EtOAc) gave the ester 2-8 as a white solid.

TLC R_f=0.19 (EtOAc). ¹H NMR (300 MHz, CD₃OD) 8.05 (s, 1H), 7.96 (dd, J=1 Hz, 8 Hz, 1H), 7.78 (dd, J=1 Hz, 8 Hz, 2H), 7.59 (d, J=8 Hz, 1H), 7.44 (m, 3H), 4.57 (s, 2H), 4.10 (t, J=8 Hz, 1H), 3.66 (t, J=6 Hz, 2H), 3.55 (m, 2H), 3.31 (t, J=6 Hz, 2H), 1.24 (s, 9H), 1.18 (s, 9H).

2-(1-Guanidoethyl)-1-isoindolone-6-carbonyl-2(S)-phenylsulfonylamino-β-alanine (2-10)

A solution of ester 2-8 (300 mg, 0.5257 mmole), TFA (3 ml) and CH₂Cl₂ (3 ml) was stirred at ambient temperature for 4.0 h. The reaction was concentrated and then azeotroped with toluene. The residue was dissolved in a solution of 2 ml DMF and 2 ml H₂O and then treated with DIPEA (276 μl, 1.58 mmole) and guanidine 2-9 (116 mg, 0.7885 mmole). The solution was heated to 60° C. for 1.0 h and then concentrated. Flash chromatography (silica, 5:1:1 EtOH/NH₄OH/H₂O) gave the crude guanidine (100 mg). Flash chromatography (silica, 10:1:1 EtOH/NH₄OH/H₂O→10:1:1 MeOH/NH₄OH/H₂O) gave the guanidine 2-10 as a white solid.

TLC R_f=0.11 (10:1:1 EtOH/NH₄OH/H₂O). ¹H NMR (400 MHz, CD₃OD) δ8.11 (s, 1H), 8.02 (d, J=9 Hz, 1H), 7.81 (d, J=6 Hz, 2H), 7.67 (d, J=8 Hz, 1H), 7.44 (m, 3H), 4.66 (s, 2H), 4.21 (m, 1H), 3.83 (t, J=6 Hz, 2H), 3.74 (m, 1H), 3.53 (m, 3H).

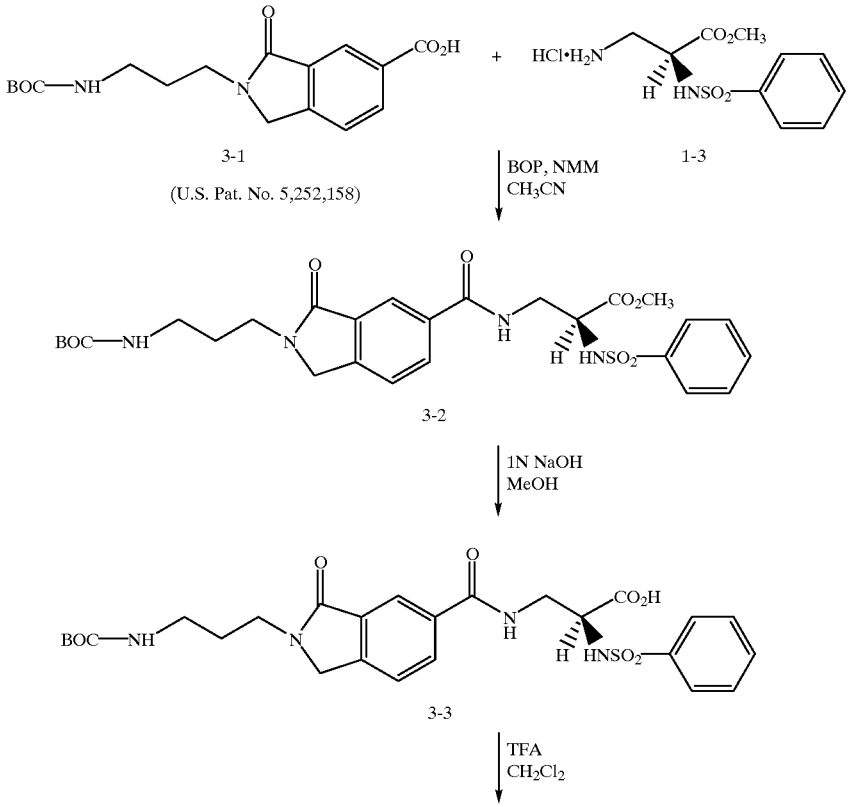

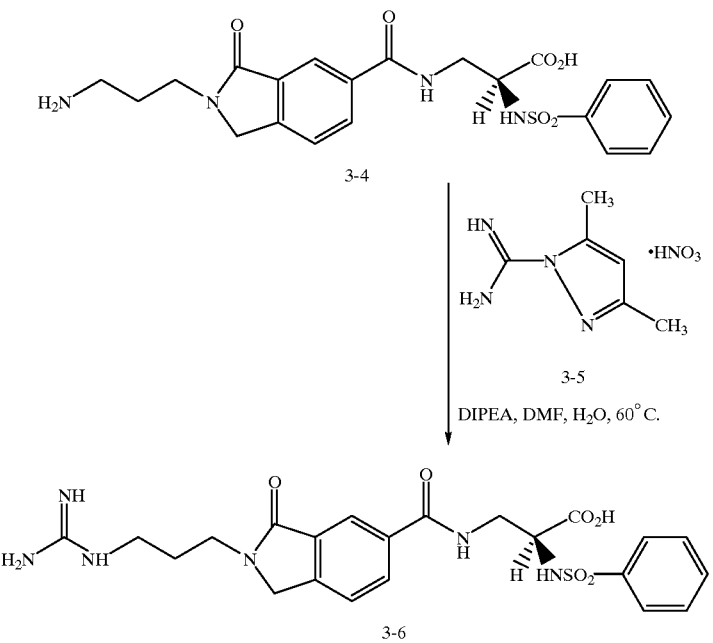

[3-(N-t-Butyloxycarbonylamino)propyl]-1-isoindolone-6-carbonyl-2(S)-phenylsulfonyl amino-β-alanine methyl ester (3-2)

A solution of acid 3-1 (120 mg, 0.3589 mmole), amine 1-3 (126 mg, 0.4307 mmole), BOP (191 mg, 0.4307 mmole), NMM (158 μl, 1.44 mmole) and $CH_3CN$ (2 ml) was stirred at ambient temperature for 20 h. The reaction was diluted with EtOAc and then washed with $H_2O$, sat. $NaHCO_3$, 10% $KHSO_4$, brine, dried ($MgSO_4$) and concentrated. Flash chromatography (silica, EtOAc) gave the ester 3-2 as a white solid.

TLC $R_f$=0.22 (Ethyl acetate). $^1H$ NMR (300 MHz, $CDCl_3$) 8.15 (s, 1H), 8.05 (dd, J=1 Hz, 8 Hz, 1H), 7.84 (dd, J=2 Hz, 7 Hz, 2H), 7.52 (m, 4H), 7.10 (bs, 1H), 6.05 (bd, 1H), 5.30 (bs, 1H), 4.45 (s, 2H), 4.13 (m, 1H), 3.80 (m, 2H), 3.71 (t, J=6 Hz, 2H), 3.62 (s, 3H), 3.14 (m, 2H), 1.85 (m, 2H), 1.42 (s, 9H).

[3-(N-t-Butyloxycarbonylamino)propyl]-1-isoindolone-6-carbonyl-2(S)-phenylsulfonylamino-β-alanine (3-3)

A solution of ester 3-2 (135 mg, 0.2421 mmole), 1 N NaOH (800 μl, 0.800 mmole), and MeOH (1.2 ml) was stirred at ambient temperature for 1.0 h. The reaction was acidified with 10% $KHSO_4$ and then extracted with EtOAc. The EtOAc portion was washed with brine, dried ($MgSO_4$) and concentrated to furnish acid 3-3 as a white solid.

TLC $R_f$=0.27 (9:1:1 $CH_2Cl_2$/MeOH/AcOH).

3-(1-Aminopropyl)-1-isoindolone-6-carbonyl-2(S)-phenylsulfonyl-amino-β-alanine (3-4)

A solution of acid 3-3 (130 mg, 0.2332 mmole), TFA (1.0 ml) and $CH_2Cl_2$ (1.0 ml) was stirred at ambient temperature for 1.0 h. The reaction was concentrated and then azeotroped with toluene. Flash chromatography (silica, 10:1:1 EtOH/$NH_4OH$/$H_2O$) gave the amine 3-4 as a white solid.

TLC $R_f$=0.27 (10:1:1 EtOH/$NH_4OH$/$H_2O$). $^1H$ NMR (300 MHz, $D_2O$ with DCl added) 7.74 (m, 5H), 7.25 (m, 3H), 4.65 (s, 2H), 4.30 (m, 1H), 3.80 (m, 1H), 3.75 (t, J=7 Hz, 2H), 3.50 (m, 1H), 3.04 (t, J=7 Hz, 2H), 2.09 (m, 2H).

3-(1-Guanidopropyl)-1-isoindolone-6-carbonyl-2(S)-phenylsulfonylamino-β-alanine (3-6)

A solution of amine 3-4 (40 mg, 0.0867 mmole), guanidine 3-5 (52 mg, 0.2601 mmole), DIPEA (45 μl, 0.2601 mmole), DMF (500 μl) and $H_2O$ (500 μl) was heated to 60° C. for 2.0 h. The reaction was concentrated. Flash chromatography (silica, 10:1:1 EtOH/$NH_4OH$/$H_2O$) gave the guanidine 3-6 as a white solid.

TLC $R_f$=0.16 (10:1:1 EtOH/$NH_4OH$/$H_2O$). $^1H$ NMR (400 MHz, $D_2O$) 7.79 (dd, J=2 Hz, 8 Hz, 1H), 7.72 (m, 3H), 7.63 (d, J=8 Hz, 1H), 7.24 (m, 3H), 4.61 (s, 2H), 4.28 (q, J=5 Hz, 1H), 3.80 (dd, J=4 Hz, 14 Hz, 1H), 3.71 (t, J=7 Hz, 2H), 3.48 (m, 1H), 3.22 (t, J=7 Hz, 2H), 1.99 (m, 2H).

SCHEME 4

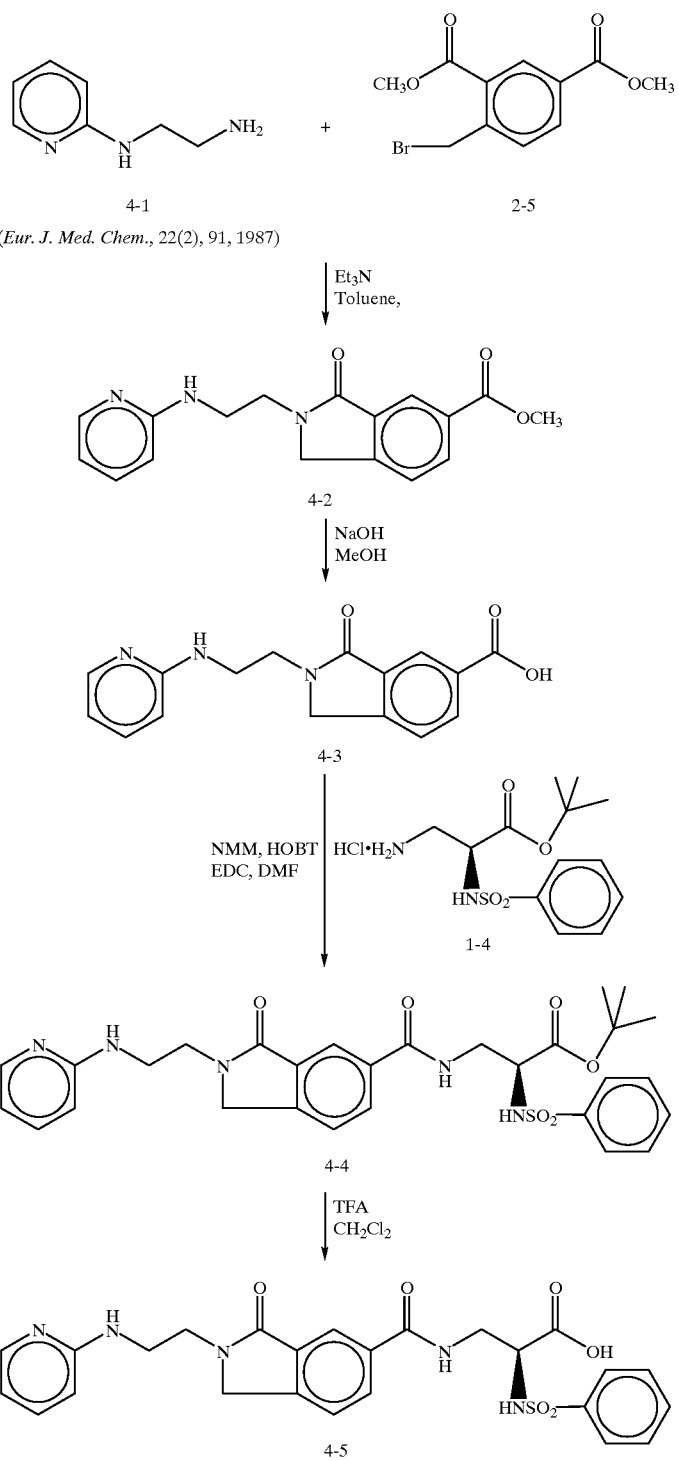

3-Oxo-2-[2-(pyridin-2-ylamino)ethyl]-2,3-dihydro-1-H-isoindole-5-carboxylic acid methyl ester (4-2)

A toluene solution (125 ml) of 4-1[1.] (1.84 g, 13.4 mmol), 2-5 (3.86 g, 13.4 mmol) and $Et_3N$ (2.8 mL, 20.1 mmol) was refluxed for 2.5 hr. and then concentrated to a solid residue which was purified by flash chromatography (silica gel, 3:2, $CH_2Cl_2$/acetone) to provide 4-2 as a colorless solid.

TLC $R_f$=0.24 (silica, 3:2 $CH_2Cl_2$/acetone). $^1$H NMR (400 MHz, $CDCl_3$) δ8.49 (s, 1H), 8.22 (dd, J=8 Hz, 1.5 Hz, 1H), 8.02 (bd, J=6 Hz, 1H), 7.49 (d, J=8 Hz, 1H), 7.34 (m, 1H), 6.51 (m, 1H), 6.41 (d, J=8 Hz, 1H), 4.83 (m, 1H), 4.53 (s, 2H), 3.95 (s, 3H), 3.90 (m, 2H), 3.71 (m, 2H).

3-Oxo-2-[2-(pyridin-2-ylamino)ethyl]-2,3-dihydro-1-H-isoindole-5-carboxylic acid (4-3)

A methanol solution (50 ml) of 4-2 (2.6 g, 8.4 mmol) and 1 N NaOH (25.2 mL, 25.2 mmol) was stirred under ambient conditions for 18 h. The reaction was concentrated and the residue acidifed with 1 M NaHSO$_4$ solution to provide 4-3 as a colorless solid.

$^1$H NMR (400 MHz, CD$_3$OD) δ8.33 (s, 1H), 8.22 (dd, J=8 Hz, 1.5 Hz, 1H), 7.89 (bd, J=6 Hz, 1H), 7.76 (m, 1H), 7.66 (d, J=8 Hz, 1H), 6.94 (d, J=9 Hz, 1H), 6.77 (m, 1H), 4.70 (s, 2H), 3.90 (t, J=6 Hz, 2H), 3.73 (d, J=6 Hz, 2H).

3-Oxo-2-[2-(pyridin-2-ylamino)ethyl]-2,3-dihydro-1H-isoindole-5-carbonyl-2(S)phenylsulfonylamino-β-alanine t-butyl ester (4-4)

A DMF solution (50 mL) of 4-3 (1.54 g, 5.2 mmol) 1-4 (2.0 g, 6.0 mnnol), HOBT (1.1 g, 7.0 mmol), NMM (2.3 mL, 21 mmol), and EDC (1.35 g, 7.0 mmol) was stirred under ambient conditions for 18 hr. The solvent was removed and the residue partitioned between EtOAc and H$_2$O. The organic layer was washed with sat. NaHCO$_3$ solution, brine and dried (MgSO$_4$). The solution was concentrated to a yellow foam which was purified by flash chromatography (silica, 1:1 CH$_2$Cl$_2$/acetone) to provide 4-4 as a yellow foam.

TLC R$_f$=0.26 (silica, 1:1 CH$_2$Cl$_2$/acetone). $^1$H NMR (400 MHz, CDCl$_3$) δ8.11 (s, 1H), 8.02 (m, 2H), 7.84 (d, J=7 Hz, 1H), 7.52 (m, 1H), 7.45 (m, 3H), 7.35 (m, 1H), 7.16 (m, 1H), 6.51 (m, 1H), 6.42 (d, J=8 Hz, 1H), 5.11 (m, 1H), 4.50 (s, 2H), 4.22 (m, 1H), 4.04, (m, 1H), 3.90 (m, 3H), 3.71 (m, 3H), 1.29 (s, 9H).

3-Oxo-2-[2-(pyridinyl-2-ylamino)ethyl]-2,3-dihydro-1H-isoindole-5-carbonyl-2(S)phenylsulfonylamino-β-alanine (4-5)

A CH$_2$Cl$_2$ solution (50 mL) of 4-4 (2.3 g, 4.0 mmol) and TFA (25 mL) was stirred tinder ambient conditions for 3 h. The reaction was concentrated and the gummy residue purified by flash chromatography (silica, 19:1 EtOH/NH$_4$OH) to provide 4-5 as a colorless solid.

TLC R$_f$=0.65 (silica, 19:1 EtOH/NH$_4$OH) $^1$H NMR (400 MHz, CD$_3$OD) δ8.18 (s, 1H), 8.03 (d, J=8 Hz, 1H), 7.88 (m, 1H), 7.82 (m, 2H), 7.62 (d, J=8 Hz, 1H), 7.40 (m, 1H), 7.38 (m, 3H), 6.52 (m, 2H), 3.86 (m, 2H), 3.65 (m, 4H), 3.42 (m, 1H).

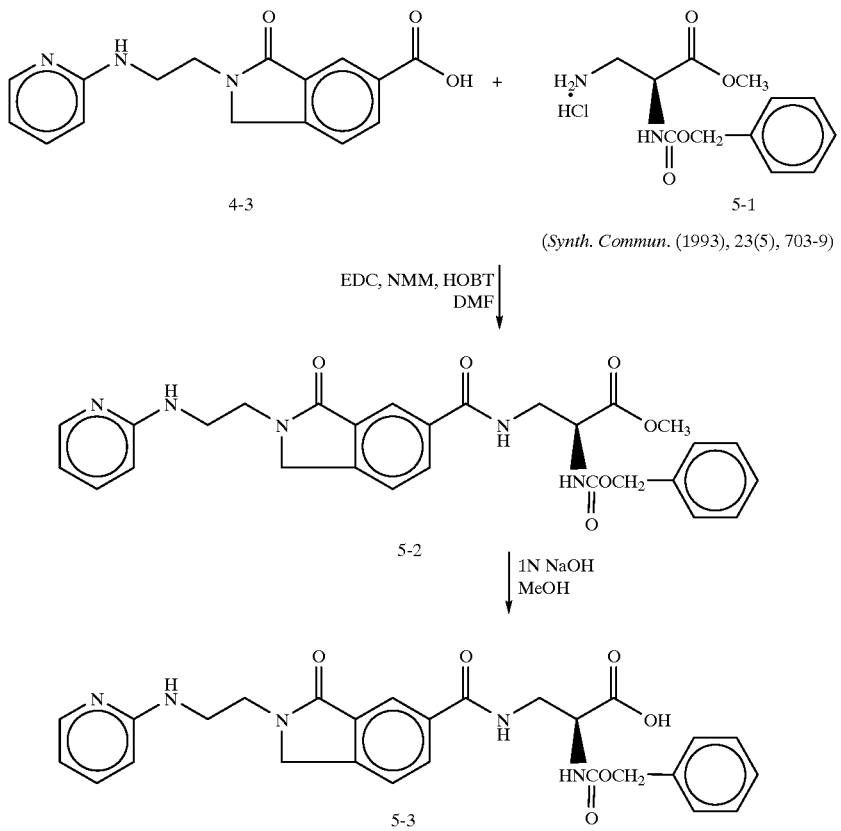

3-Oxo-2-[2-(pyridin-2-ylamino)ethyl]-2,3-dihydro-1H-isoindole-5-carbonyl-2(S) benzyloxycarbonylamino-β-alanine methyl ester (5-2)

A DMF solution (5 mL) of 4-3 (297 mg, 1.0 mmol), 5-1 (346 mg, 1.2 mmol), HOBT (206 mg, 1.35 mmol) NMM (440 ml, 4.0 mmol) and EDC (259 mg, 1.35 mmol) was stirred under ambient conditions for 18 h. The solvent was removed and the residue partitioned between EtOAc and H$_2$O. The organic layer was washed with H$_2$O, sat. NaHCO$_3$ solution, brine and dried (MgSO$_4$). The filtrate was concentrated to a pale yellow foam which was purified by flash chromatography (silica, 2:3 CH$_2$Cl$_2$/acetone) to provide 5-2 as a foam.

TLC R$_f$=0.27 (silica, 2:3 CH$_2$Cl$_2$/acetone). $^1$H NMR (400 MHz, CDCl$_3$) δ8.03 (m, 3H), 7.41 (m, 2H), 7.26–7.34 (m, 6H), 6.51 (m, 1H), 6.38 (d, J=8 Hz, 1H), 6.32 (m, 1H), 5.12 (m, 1H), 5.07 (bs, 2H), 4.58 (m, 1H), 4.44 (m, 2H), 3.86 (m, 4H), 3.78 (s, 3H), 3.68 (m, 2H).

3-Oxo-2-[2-pyridin-2-ylamino)ethyl]-2,3-dihydro-1H-isoindole-5-carbonyl-2(S)-benzoyloxycarbonylamino-β-alanine (5-3)

A methanol solution (25 mL) of 5-2 (328 mg, 0.61 mmol) and 1N NaOH (5 mL, 5 mmol) was stirred under ambient conditions overnight. The reaction was concentrated to dryness and the residue dissolved in H$_2$O and the solution acidified with 6 N HCl to provide 5-3 as a solid.

$^1$H NMR (400 MHz, CD$_3$OD) δ8.14 (s, 1H), 8.04 (d, J=8 Hz, 1H), 7.87 (m, 2H), 7.66 (d, J=8 Hz, 1H), 7.23–7.34 (m, 5H), 7.04 (d, J=9 Hz, 1H), 6.89 (dd, J=7 Hz, 7 Hz, 1H), 5.07 (m, 2H), 4.68 (s, 2H), 4.51 (m, 1H), 3.94 (t, J=6 Hz, 2H), 3.87 (m, 1H), 3.75 (m, 3H).

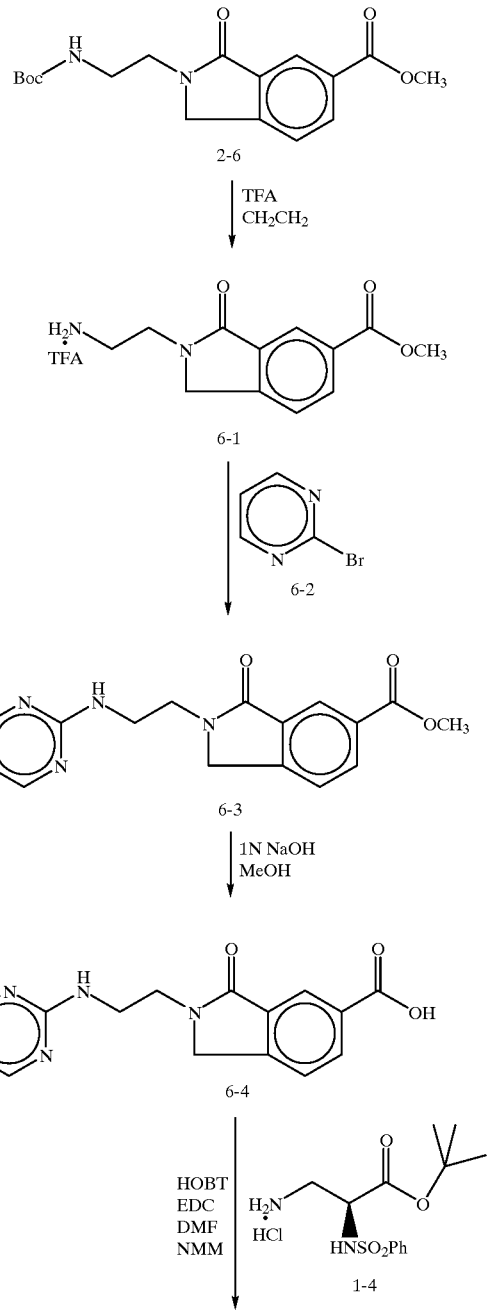

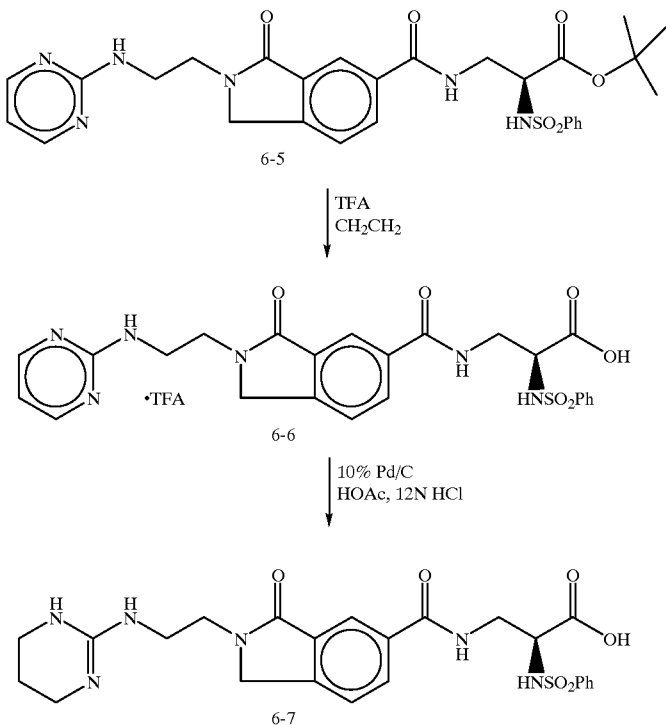

3-Oxo-2-(2-aminoethyl)-2,3-dihydro-1-H-isoindole-5-carboxylic acid methyl esther trifluoroacetate (6-1)

The ester 2-6 and TFA (5 mL) were dissolved in CH₂Cl₂ (25 mL) and the solution stirred under ambient conditions for 18 h. The solution was concentrated to dryness and the residue was azeotroped with toluene (3×25 mL) to provide 6-1 as a cream-colored solid.

$^1$H NMR (400 MHz, CD$_3$OD) δ8.42 (s, 1H), 8.29 (d, J=8 Hz, 1H), 7.72 (d, J=8 Hz, 1H), 4.66 (s, 2H), 3.96 (s, 3H), 3.91–3.96 (m, 4H).

3-Oxo-2-[2-(pyrimidin-2-ylamino)ethyl]-2,3-dihydro-1H-isoindole-5-carboxylic acid methyl ester (6-3)

A DMF solution (10 mL) containing 6-1 (870 mg, 2.5 mmol) diisopropylethylamine (1.3 mL, 7.5 mmol) and 6-2 (472 mg, 2.97 mmol) was stirred at 100° C. for 18 hr. The DMF was removed at 50° C. and the residue partitioned between EtOAc and H₂O. The organic layer was washed with brine and dried (MgSO₄). Evaporation gave a solid which was purified by flash chromatography (silica, 19:1 EtOAc/MeOH) to yield 6-3 as a cream-colored solid.

TLC R$_f$=0.18 (19:1, EtOAc/MeOH). $^1$H NMR (400 MHz, CDCl$_3$) δ8.50 (s, 1H), 8.25 (m, 3H), 7.49 (d, J=8 Hz, 1H), 6.52 (dd, J=5 Hz, 5 Hz, 1H), 4.54 (s, 2H), 3.96 (s, 3H), 3.90 (m, 2H), 3.77 (m, 2H).

3-Oxo-2-[2-(pyrimidin-2-ylamino)ethyl]-2,3-dihydro-1H-isoindole-5-carboylic acid (6-4)

A methanol solution (25 mL) of ester 6-3 (400 mg, 1.28 mmol) and 1 N NaOH (5 mL, 5 mmol) was stirred under ambient conditions for 18 hr. The reaction solution was concentrated to dryness and the residue was neutralized with 1 M NaHSO₄ solution to provide 6-4 as a pale yellow solid.

$^1$H NMR (400 MHz, CD$_3$OD/NaOD) δ8.29 (s, 1H), 8.18 (m, 3H), 7.53 (d, J=8 Hz, 1H), 6.53 (dd, J=5 Hz, 5 Hz, 1H), 5.18 (s, 2H), 3.86 (m, 2H), 3.72 (m, 2H).

3-Oxo-2-[2-(pyrimidin-2-ylamino)ethyl]-2,3-dihydro-1H-isoindole-5-carbonyl-2(S)phenylsulfonylamino-β-alanine t-butyl ester (6-5)

A DMF solution (10 mL) of acid 6-4 (382 mg, 1.28 mmol) 1-4 (517 mg, 1.54 mmol), HOBT (264 mg, 1.13 mmol) NMM (563 μl, 5.1 mmol) and EDC (331 mg, 1.73 mmol) was stirred under ambient conditions for 18 h. The DMF was removed at 50° C. and the residue partitioned between EtOAc and H₂O. The organic layer was washed with sat. NaHCO₃ solution, brine, and dried (MgSO₄). Evaporation gave a yellow foam which was purified by flash chromatography (silica, 3:1 acetone/CH₂Cl₂) to provide 6-5 as a colorless foam.

TLC R$_f$=0.29 (silica, 3:1 acetone/CH$_2$Cl$_2$). $^1$H NMR (400 MHz, CDCl$_3$) δ8.23 (m, 2H), 8.14 (s, 1H), 8.02 (d, J=8 Hz, 2H), 7.40–7.54 (m, 4H), 6.49 (m, 2H), 5.96 (m, 1H), 4.51 (m, 2H), 4.06 (m, 1H), 3.95 (m, 1H), 3.62–3.88 (m, 5H), 1.26 (s, 9H).

3-Oxo-2-[2-(pyrimidin-2-ylamino)ethyl]-2,3-dihydro-1-H-isoindole-5-carbonyl-2(S)phenylsulfonylamino-β-alanine trifluoroacetate (6-6)

A CH₂Cl₂ solution (50 mL) of 6-5 (588 mg, 1.01 mmol) and TFA (5 mL) was stirred under ambient conditions for 18 hr. The solution was concentrated and the residue triturated with toluene (3×25 mL) to provide 6-6 as a tan form.

TLC R$_f$=0.08 (silica, 3:1 acetone/CH$_2$Cl$_2$). $^1$H NMR (400 MHz, CD$_3$OD) δ8.39 (bs, 1H), 8.01 (m, 2H), 7.83 (d, J=8 Hz, 2H), 7.65 (d, J=8 Hz, 1H), 7.44 (m, 3H), 7.20 (m, 1H), 6.79 (dd, J=5 Hz, 5 Hz, 1H), 4.68 (s, 2H), 4.23 (m, 1H), 3.93 (m, 2H), 3.84 (m, 2H), 3.78 (m, 1H), 3.50 (m, 1H).

3-Oxo-2-[2-(3,4,5,6-tetrahydropyrimidin-2-ylamino)ethyl]-1-H-isoindole-5-carbonyl-2(S)phenylsulfonylamino-β-alanine (6-7)

10% Pd/C (101 mg) was added to HOAc/12 0 N HCl solution (19:1, 31 ml) containing 6-6 (649 mg, 1.01 mmol) and the mixture hydrogenated at 60 PSI for 2.5 hr. Filtration and concentration gave a gum which was purified by flash chromatography (silica, 7:1.5:1.5 EtOH/NH₄OH/H₂O) to provide 6-7 as a colorless solid.

TLC $R_f$=0.36 (silica, 7:1.5:1.5 EtOH/NH$_4$OH/H$_2$O). $^1$H NMR (400 MHz, CD$_3$OD) δ7.86 (m, 2H), 7.74 (m, 2H), 7.67 (m, 1H), 7.31 (m, 3H), 4.65 (s, 2H), 3.96 (m, 1H), 3.81 (m, 2H), 3.73 (m, 1H), 3.50 (m, 2H), 3.43 (m, 1H), 3.20 (m, 4H), 1.72 (m, 2H).
SCHEME 7
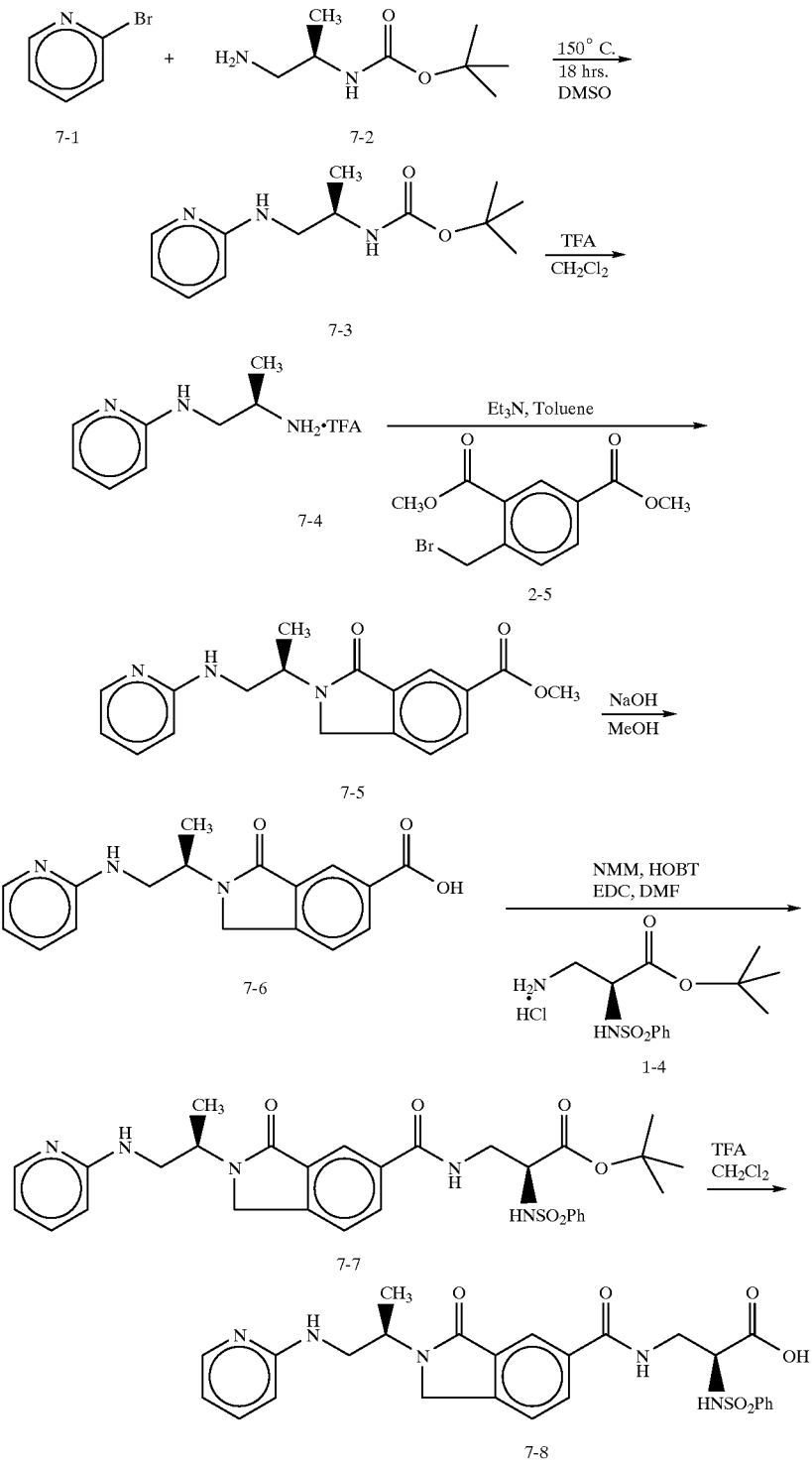

[1(R) Methyl-2-(pyridin-2-yl)ethyl]carbamic acid t-butylester (7-3)

A DMSO solution (1 mL) of 7-1 (95 µl, 1.0 mmol), 7-2[1]. (191 mg, 1.1 mmol) was heated at 140° C. for 18 h. Removal of the DMSO gave a residue which was purified by flash chromatography (silica, 3:2 EtOAc/hexane) to provide 7-3 as a viscous gum.

[1]. U.S. Pat. No. 5,272,175, G. D. Searle and Co., Dec. 21, 1993.

TLC $R_f$=0.29 (silica, 3:2 EtOAc/hexane). $^1$H NMR (400 MHz, CDCl$_3$) δ8.05 (bd, J=5 Hz, 1H), 7.37 (m, 1H), 6.54 (m, 1H), 6.41 (d, J=8 Hz, 1H), 4.90 (m, 2H), 3.98 (m, 1H), 3.36 (m, 2H), 1.47 (s, 9H), 1.20 (d, J=7 Hz, 3H).

[1(R) Methyl-2-(pyridin-2-yl)ethyl]carbamic acid trifluoroacetate (7-4)

TFA (4 mL) was added to a CH$_2$Cl$_2$ solution (10 mL) of 7-3 (120 mg, 0.48 mmol) and the solution stirred under ambient conditions for 2 h and concentrated to dryness. The residue was azeotroped with toluene (3×25 mL) to provide 7-4 as a light-yellow semi-solid.

$^1$H NMR (400 MHz, CD$_3$OD) δ7.98 (bd, J=5 Hz, 1H), 7.88 (m, 1H), 7.01 (d, J=9 Hz, 1H), 6.91 (m, 1H), 3.59 (m, 3H), 1.38 (d, J=7 Hz, 3H).

3-Oxo-2-[1(R)-methyl-2(pyridinyl)-2-yl)ethyl]-2,3-dihydro-1-H-isoindole-5-carboxylic acid methyl ester (7-5)

A toluene solution (20 mL) of 7-4 (181 mg, 0.48 mmol), 2-5 (171 mg, 0.60 mmol) and Et$_3$N (266 µl, 1.9 mmol) was refluxed for 3 h and then concentrated to dryness. The residue was purified by flash chromatography (silica, 3:2 CH$_2$Cl$_2$/acetone) to provide 7-5 as a colorless gum.

TLC $R_f$=0.40 (silica, 3:2 CH$_2$Cl$_2$/acetone). $^1$H NMR (400 MHz, CDCl3) δ8.43 (bs, 1H), 8.15 (bd, J=8 Hz, 1H), 7.96 (bd, J=5 Hz, 1 Hz) 7.46 (d, J=8 Hz, 1H), 7.26 (m, 1H), 6.44 (m, 1H), 6.35 (d, J=8 Hz, 1H), 4.81 (m, 1H), 4.75 (m, 1H), 4.44 (q, J=39 Hz, 18 Hz, 2H), 3.94 (s, 3H), 3.81 (m, 1H), 3.46 (m, 1H), 1.41 (d, J=7 Hz, 3H).

3-Oxo-2-[1(R)-methyl-2(pyridinyl-2-yl)ethyl]-2,3-dihydro-1-H-isoindole-5-carboxylic acid (7-6)

A methanol solution (5 mL) of 7-5 (58 mg, 0.18 mmol) and 1 N NaOH (2 mL, 2.0 mmol) was stirred under ambient conditions for 5 h and then concentrated to dryness. The residue was dissolved in H$_2$O (2 mL) and the solution neutralized with 1 M NaHSO$_4$ solution to provide 7-6 as a colorless solid.

$^1$H NMR (400 MHz, CD$_3$OD) δ8.29 (s, 1H), 8.16 (bd, J=8 Hz, 1H), 7.84 (bd, J=4 Hz, 1H), 7.52 (d, J=8 Hz, 1H), 7.33 (m, 1H), 6.46 (m, 2H), 5.01 (s, 2H), 4.66 (m, 1H), 3.58 (m, 2H), 1.38 (d, J=7 Hz, 3H).

3-Oxo-2-[1(R)-methyl-2(pyridin-2-yl)ethyl]-2,3-dihydro-1-H-isoindole-5-carbonyl-2(S)phenylsulfonylamino-β-alanine t-butyl ester (7-7)

A DMF solution (5 mL) of acid 7-6 (55.4 mg, 0.178 mmol), 1.4 (72 mg, 0.213 mmol), HOBT (38 mg, 0.249 mmol), NMM (81 µl, 0.712 mmol) and EDC (48 mg, 0.249 mmol) was stirred under ambient conditions for 18 h. The DMF was removed at 50° C. and the residue was partitioned between EtOAc and H$_2$O. The organic layer was washed with sat. NaHCO$_3$ solution, brine and dried (MgSO$_4$). Filtration and evaporation gave a yellow solid which was purified by flash chromatography (silica, 3:1 acetone/CH$_2$Cl$_2$) to provide 7-7 as a colorless solid.

TLC $R_f$=0.33 (silica; 1:1 acetone/CH$_2$Cl$_2$). $^1$H NMR (400 MHz, CDCl$_3$) δ8.13 (s, 1H), 8.00 (d, J=8 Hz, 1H), 7.96 (d, J=5 Hz, 1H), 7.85 (d, J=7 Hz, 2H), 7.28 (m, 1H), 7.54 (m, 1H), 7.49 (m, 3H), 6.90 (m, 1H), 6.44 (m, 1H), 6.39 (d, J=8 Hz, 1H), 5.81 (m, 1H), 4.88 (m, 1H), 4.76 (m, 1H), 4.44 (dd, J=42 Hz, 17 Hz, 2H), 3.98 (m, 1H), 3.91 (m, 1H), 3.81 (m, 1H), 3.64 (m, 1H), 3.46 (m, 1H), 1.41 (d, J=7 Hz, 3H), 1.29 (s, 9H).

3-Oxo-2-[1(R)-methyl-2(pyridin-2-yl)ethyl]-2,3-dihydro-1-H-isoindole-5-carbonyl-2(S)phenylsulfonylamino-β-alanine (7-8)

A CH$_2$Cl$_2$ solution (20 mL) of 7-7 (44 mg, 0.074 mmol) and TFA (4 mL) was stirred under ambient conditions for 5 h and then concentrated. The residue was azeotroped with toluene (3×25 mL) to give a solid which was purified by HPLC using a VYDAC C$_{18}$ semiprep column with gradient elution [95:5 (99.9:0.1 H$_2$O/TFA)/(99.9:0.1 CH$_3$CN/TFA) →50:50 (99.9:1 H$_2$O/TFA) (99.9:1 CH$_3$CN/TFA) 60 min] to provide 7-8 as a colorless solid.

$^1$H NMR (400 MHz, CD$_3$OD) δ8.10 (s, 1H), 8.05 (bd, J=7 Hz, 1H), 7.88 (m, 2H), 7.83 (d, J=7 Hz, 2H), 7.69 (d, J=8 Hz, 1H), 7.45 (m, 3H), 7.02 (m, 1H), 6.90 (m, 1H), 4.71 (m, 1H), 4.62 (s, 2H), 4.22 (m, 1H), 3.77 (m, 1H), 3.65 (m, 2H), 3.50 (m, 1H), 1.48 (d, J=7 Hz, 3H).

SCHEME 8

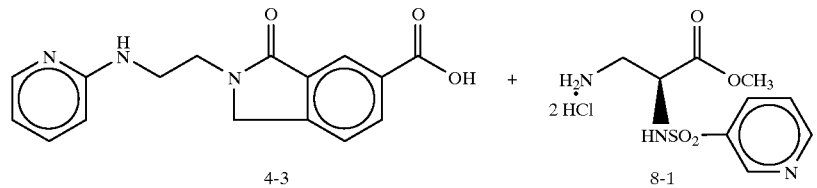

(U.S. Pat. No. 5,397,791)

EDC, NMM, HOBT
DMF

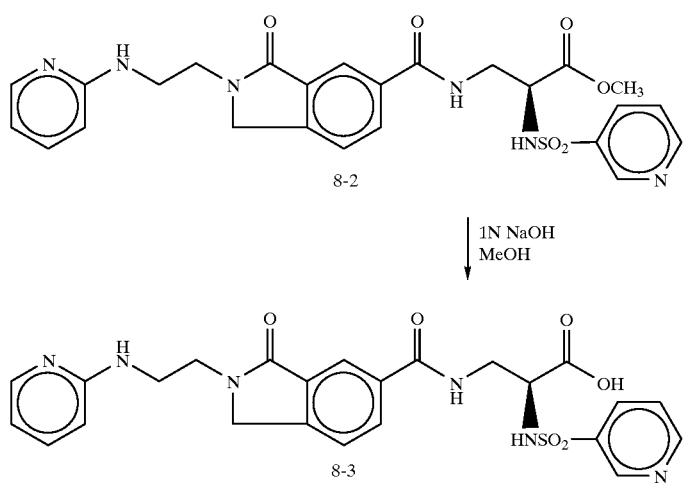

3-Oxo-2[2-(pyridin-2-ylamino)ethyl]-2,3-dihydro-1H-isoindole-5-carbonyl-2(S)-(3-pyridinylsulfonylamino)-β-alanine methyl ester (8-2)

A DMF solution (10 mL) of 4-3 (297 mg, 1.0 mmol), 8-1 (398 mg, 1.2 mmol), HOBT (206 mg, 1.35 mmol) NMM (440 ml, 4.0 mmol) and EDC (259 mg, 1.35 mmol) was stirred under ambient conditions for 18 h. The solvent was removed and the residue partitioned between EtOAc and $H_2O$. The organic layer was washed with sat. $NaHCO_3$ solution, brine and dried ($MgSO_4$). The filtrate was concentrated to a yellow foam which was purified by flash chromatography (silica, 19:1 $CH_2Cl_2$/MeOH) to provide 8-2 as a colorless foam.

TLC $R_f$=0.08 (silica, 19:1 $CH_2Cl_2$/MeOH). $^1$H NMR (400 MHz, $CDCl_3$) δ9.03 (d, J=2 Hz, 1H), 8.66 (d, J=5 Hz, 1H), 8.02–8.04 (m, 2H), 7.95 (d, J=8 Hz, 1H), 7.89 (s, 1H), 7.54 (bs, 1H), 7.30–7.37 (m, 2H), 7.26 (m, 2H), 6.59 (m, 1H), 6.42 (d, J=8 Hz, 1H), 5.30 (m, 1H), 4.44 (m, 2H), 4.36 (m, 1H), 4.04–3.67 (m, 6H), 3.65 (s, 3H).

3-Oxo-2[2-pyridin-2-ylamino)ethyl]-2,3-dihydro-1H-isoindole-5-carbonyl-2(S)-(3-pyridinyisulfonylamino)-β-alanine (8-3)

A methanol solution (3 mL) of 8-2 (184 mg, 0.34 mmol) and 1 N NaOH (3.4 mL, 3.4 mmol) was stirred under ambient conditions for 3 h. The reaction was concentrated to dryness and the residue dissolved in $H_2O$ and neutralized with 1 N HCl to provide 8-3 as a solid.

$^1$H NMR (400 MHz, $CD_3OD$) δ8.94 (bs, 1H), 8.41 (d, J=5 Hz, 1H), 8.21 (d, J=8 Hz, 1H), 8.18 (bs, 1H), 8.03 (d, J=8 Hz, 1H), 7.88 (d, J=5 Hz, 1H), 7.62 (d, J=8 Hz, 1H), 7.36 (m, 2H), 6.51 (m, 2H), 5.10 (m, 2H), 3.86 (m, 2H), 3.66 (m, 4H), 3.46 (m, 1H).

EXAMPLE OF A PHARMACEUTICAL FORMULATION

As a specific embodiment of an oral composition, 100 mg of compound 2-10 is formulated with sufficient finely divided lactose to provide a total amount of 580 to 590 mg to fill a size O hard gel capsule.

The test procedures employed to measure αvβ3 binding and the bone resorption inhibiting activity of the compounds of the present invention are described below.

BONE RESORPTION-PIT ASSAY

When osteoclasts engage in bone resorption, they will literally cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a six mm cylinder of bovine femur diaphysis were cut with a low speed diamond saw (Isomet, Beuler, Ltd., Lake Bluff, Ill.). Bone slices were pooled, placed in a 10% ethanol solution and refrigerated until further use.

Prior to experimentation, bone slices were ultrasonicated twice, 20 minutes each in $H_2O$. Cleaned slices were placed in 96 well plates such that two control lanes and one lane for each drug dosage are available. Each lane represents either triplicate or quadruplicate cultures. The bone slices in 96 well plates were sterilized by UV irradiation. Prior to incubation with osteoclasts, the bone slices were hydrated by the addition of 0.1 ml Medium 199, pH 6.9 containing 15% fetal bovine serum and 1% penicillin/streptomycin.

Osteoclasts were isolated from the long bones of 1 to 3 day old rat pups (Sprague-Dawley) by modifications of Chambers et al., (J. Cell. Science, 66:383–399). The resulting suspension (0.75 ml/bone) was gently triturated 90–120 times using a wide bore transfer pipet. The cellular population was separated from bone fragments by a cell strainer with a 100 micron nylon mesh. 100 μl of the cell suspension was placed onto each bone slice. Test compounds were then added at the desired experimental concentrations.

Bone slices exposed to osteoclasts for 20–24 hrs were processed for staining. Tissue culture media was removed from each bone slice. Each well was washed with 200 μl of $H_2O$, and the bone slices were then fixed for 20 minutes in 2.5% glutaraldehyde, 0.1 M cacodylate, pH 7.4. After fixation, any remaining cellular debris was removed by 2 min. ultrasonication in the presence of 0.25 M $NH_4OH$ followed by 2×15 min ultrasonication in $H_2O$. The bone slices were immediately stained for 6–8 min with filtered 1% toluidine blue and 1% borax.

After the bone slices have dried, resorption pits were counted in test and control slices. Resorption pits were viewed in a Microphot Fx (Nikon) fluorescence microscope using a polarizing Nikon IGS filter cube. Test dosage results were compared with controls and resulting $IC_{50}$ values were determined for each compound tested.

The appropriateness of extrapolating data from this assay to utility and use in mammalian (including human) disease states is supported by the teaching found in Sato, M., et al., *Journal of Bone and Mineral Research*, Vol. 5, No. 1, 1990. That article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8:S 378, describe a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption. Reaction Mixture:

1. 175 µl TBS buffer (50 mM Tris.HCl pH 7.2, 150 mM NaCl, 1% BSA, 1 mM CaCl$_2$, 1 mM MgCl$_2$).
2. 25 µl cell extract (dilute with 100 mM octylglucoside buffer to give 2000 cpm/25 µl).
3. $^{125}$I-echistatin (25 µl/50,000 cpm) (see EP 382 451).
4. 25 µl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% polyethyleneimine for 10 mins) were then washed with the wash buffer (50 mM Tris HCl, 1 mM CaCl$_2$/MgCl$_2$, pH 7.2). The filter was then counted in a gamma counter.

OCFORM ASSAY

Osteoblast-like cells (1.8 cells), originally derived from mouse calvaria, were plated in CORNING 24 well tissue culture plates in α MEM medium containing ribo-and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 µm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at 1×10$^6$ cells/mL. 50 µL was added to each well of 1.8 cells to yield 50,000 cells/well and 1,25-dihydroxy-vitamin D$_3$(D$_3$) was added to each well to a final concentration of 10 nM. The cultures were incubated at 37° C. in a humidified, 5% CO$_2$ atmosphere. After 48 h, the medium was changed. 72 h after the addition of bone marrow, test compounds were added with fresh medium containing D$_3$ to quadruplicate wells. Compounds were added again after 48 h with fresh medium containing D$_3$. After an additional 48 h the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells were counted in each well.

Representative compounds of the present invention were tested and found to bind to human αvβ3 integrin. These compounds were found to have IC$_{50}$ values in the range of 0.7–415 nM for the EIB assay.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

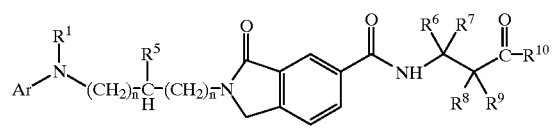

wherein Ar is

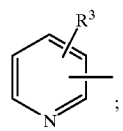

R$^1$ and R$^3$ are each independently selected from hydrogen, hydroxyl, C$_{1-8}$ alkyl, halogen, aryl C$_{0-8}$ alkyl, oxo, thio, amino-C$_{0-8}$ alkyl, C$_{1-3}$ acylamino C$_{0-8}$ alkyl, C$_{1-6}$ alkylamino C$_{0-8}$ alkyl, C$_{1-6}$ dialkylamino C$_{0-8}$ alkyl, aryl C$_{0-6}$ alkylamino C$_{0-6}$ alkyl, C$_{1-4}$ alkoxyamino C$_{0-8}$ alkyl, hydroxy C$_{1-6}$ alkylamino C$_{0-8}$ alkyl, C$_{1-4}$ alkoxy C$_{0-8}$ alkyl, carboxy C$_{0-8}$ alkyl, C$_{1-4}$ alkoxycarbonyl C$_{0-8}$ alkyl, carboxy C$_{0-8}$ alkoxy, hydroxy C$_{0-8}$ alkyl or C$_{3-8}$ cycloalkyl C$_{0-6}$ alkyl;

R$^5$ is selected from hydrogen, C$_{1-6}$ alkyl, C$_{0-6}$ alkylaryl, aryl or C$_{3-8}$ cycloalkyl C$_{0-6}$ alkyl;

R$^6$, R$^7$, R$^8$ and R$^9$ are each independently selected from hydrogen, fluorine, C$_{1-8}$ alkyl, hydroxyl, hydroxy C$_{1-6}$ alkyl, carboxy $C_{0-6}$ alkyl, $C_{1-6}$ alkoxy, $C_{1-6}$ alkylcarbonyl, aryl $C_{0-6}$ alkylcarbonyl, $C_{1-6}$ alkylcarbonyloxy, aryl $C_{0-6}$ alkylcarbonyloxy, $C_{1-6}$ alkylamino-carbonyloxy, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{0-8}$ alkyl-$SO_2NR^3$—$C_{0-8}$ alkyl, aryl $C_{0-8}$ alkoxycarbonylamino $C_{0-8}$ alkyl, aryl-$C_{0-8}$ alkyl-$SO_2NR^3$—$C_{0-8}$ alkyl, $C_{1-8}$ alkoxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{0-8}$ alkylaminosulfonylamino $C_{0-6}$ alkyl, aryl $C_{0-8}$ alkylaminosulfonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl, aryl $C_{0-6}$ alkylcarbonyl $C_{0-6}$ alkyl, $C_{1-6}$ alkylthiocarbonylamino $C_{0-6}$ alkyl, aryl $C_{0-6}$ alkylthiocarbonylamino $C_{0-6}$ alkyl, $C_{3-8}$ cycloalkyl $C_{0-6}$ alkyl, $C_{3-8}$ cycloalkyl $C_{0-6}$ alkylsulfonylamino $C_{0-6}$ alkyl, $C_{3-8}$ cycloalkyl-$C_{0-6}$ alkylcarbonyl, $C_{3-8}$ cycloalkyl $C_{0-6}$ alkylaminocarbonyloxy or $C_{3-8}$ cycloalkyl $C_{0-6}$ alkylaminocarbonylamino; wherein any of the alkyl groups may be unsubstituted or substituted with $R^1$ and $R^2$;

$R^{10}$ is selected from hydroxyl, $C_{1-8}$ alkoxy, aryl $C_{0-6}$ alkoxy, $C_{1-8}$ alkylcarbonyloxy $C_{1-4}$ alkoxy, aryl $C_{1-8}$ alkylcarbonyloxy $C_{1-4}$ alkoxy, $C_{1-6}$ dialkylaminocarbonylmethoxy, aryl $C_{1-6}$ dialkylaminocarbonylmethoxy or an L- or D-amino acid joined by an amide linkage and wherein the carboxylic acid moiety of the amino acid is as the free acid or is esterified by $C_{1-6}$ alkyl; and each n is independently an integer from 0 to three;
and the pharmaceutically acceptable salts thereof.

2. The compound of claim 1 wherein $R^1$ and $R^3$ are each independently selected from hydrogen, $C_{1-6}$ alkyl, aryl $C_{0-6}$ alkyl, amino $C_{0-6}$ alkyl, $C_{1-6}$ alkylamino-$C_{0-6}$ alkyl, $C_{1-6}$ dialkylamino $C_{0-6}$ alkyl, $C_{1-4}$ alkoxy $C_{0-6}$ alkyl or $C_{1-4}$ alkoxycarbonyl $C_{0-6}$ alkyl;

$R^6$, $R^7$, $R^8$ and $R^9$ are each independently selected from hydrogen, $C_{1-6}$ alkyl, $C_{0-6}$ alkylamino $C_{0-6}$ alkyl, $C_{0-6}$ dialkylamino $C_{0-6}$ alkyl, aryl $C_{0-6}$ alkoxycarbonylamino $C_{0-6}$ alkyl, aryl $C_{0-6}$ alkyl-$SO_2NR^3$—$C_{0-6}$ alkyl, $C_{0-6}$ alkyl-$SO_2NR^3$—$C_{0-6}$ alkyl or aryl $C_{0-6}$ alkylcarbonylamino $C_{0-6}$ alkyl; and $R^{10}$ is selected from hydroxy, $C_{1-8}$ alkoxy, $C_{1-6}$ dialkylaminocarbonylmethoxy or aryl $C_{1-6}$ dialkylaminocarbonylmethoxy;
and the pharmaceutically acceptable salts thereof.

3. The compound of claim 2 of the formula

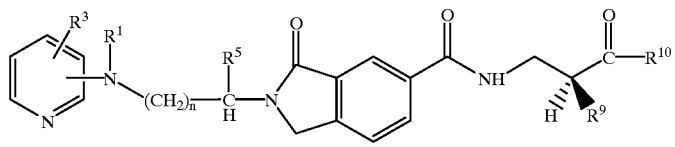

wherein $R^1$ and $R^3$ are each independently selected from hydrogen or $C_{1-6}$ alkyl;

$R^5$ is selected from hydrogen or $C_{1-6}$ alkyl;

$R^9$ is selected from

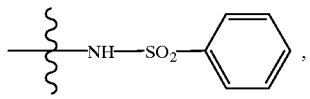,

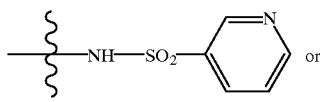 or

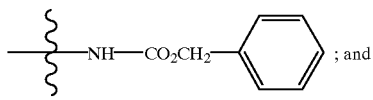 ; and $R^{10}$ is selected from hydroxy or $C_{1-6}$ alkoxy;

and the pharmaceutically acceptable salts thereof.

4. The compound of claim 3 wherein $R^5$ is selected from hydrogen or methyl; and n is an integer from 1 to 2;

and the pharmaceutically acceptable salts thereof.

5. The compound of claim 4 wherein $R^{10}$ is hydroxy;

and the pharmaceutically acceptable salts thereof.

6. The compound of claim 5 selected from

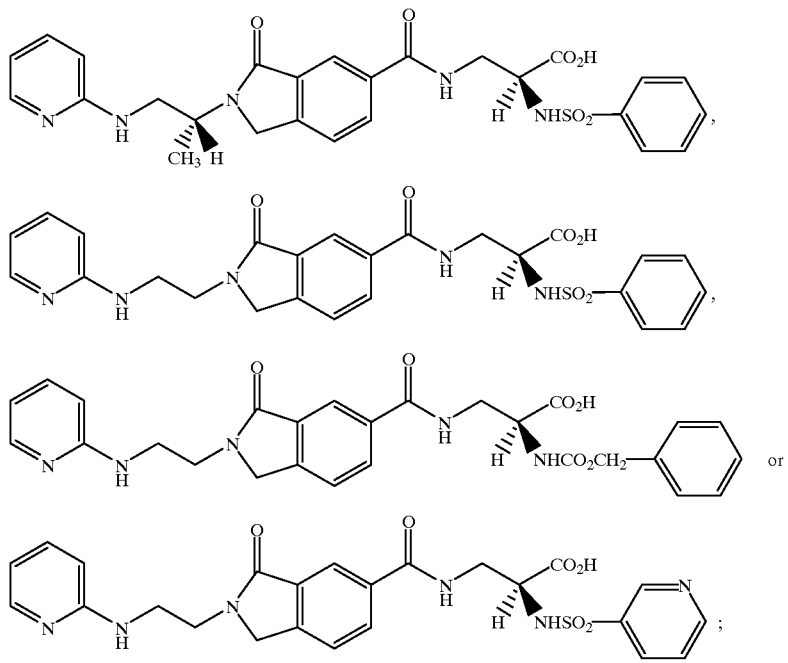

and the pharmaceutically acceptable salts thereof.

7. A pharmaceutical composition comprising an effective amount of the compound of claim 1 and a pharmaceutically acceptable carrier.

8. A pharmaceutical composition made by combining a compound of claim 1 and a pharmaceutically acceptable carrier.

9. A process for making a pharmaceutical composition comprising combining a compound of claim 1 and a pharmaceutically acceptable carrier.

10. A method of eliciting an αvβ3 antagonizing effect in a mammal in need thereof, comprising administering to the mammal a therapeutically effective amount of the compound of claim 1.

11. The method of claim 10, wherein the αvβ3 antagonizing effect is selected from inhibition of bone resorption, inhibition of restenosis, inhibition of angiogenesis, inhibition of atherosclerosis, inhibition of inflammation, inhibition of diabetic retinopathy, inhibition of macular degeneration or inhibition of tumor growth.

12. The method of claim 11, wherein the αvβ3 antagonizing effect is the inhibition of bone resorption.

13. A method of treating or preventing a condition mediated by antagonism of an αvβ3 receptor in a mammal in need thereof, comprising administering to the mammal a therapeutically effective amount of the compound of claim 1.

14. The method of claim 13, wherein the condition is selected from the group consisting of osteoporosis and cancer.

15. A method of inhibiting bone resorption in a mammal in need thereof, comprising administering to the mammal a therapeutically effective amount of the compound of claim 1.

16. A method of treating osteoporosis in a mammal in need thereof, comprising administering to the mammal a therapeutically effective amount of the compound of claim 1.

17. A method of inhibiting bone resorption in a mammal in need thereof, comprising administering to the mammal a therapeutically effective amount of the composition of claim 7.

18. A method of treating osteoporosis in a mammal in need thereof, comprising administering to the mammal a therapeutically effective amount of the composition of claim 7.

* * * * *